United States Patent
Simon et al.

(10) Patent No.: US 9,649,074 B2
(45) Date of Patent: May 16, 2017

(54) SCAN GEOMETRY CORRECTIONS FOR TOMOSYNTHESIS MOBILE RADIOGRAPHIC APPARATUS

(71) Applicant: Carestream Health, Inc., Rochester, NY (US)

(72) Inventors: Richard A. Simon, Rochester, NY (US); David H. Foos, Webster, NY (US); John Yorkston, Penfield, NY (US); Xiaohui Wang, Pittsford, NY (US)

(73) Assignee: Carstream Health, Inc., Rochester, NY (US)

( * ) Notice: Subject to any disclaimer, the term of this patent is extended or adjusted under 35 U.S.C. 154(b) by 0 days.

(21) Appl. No.: 14/435,272

(22) PCT Filed: Nov. 19, 2013

(86) PCT No.: PCT/US2013/070686
§ 371 (c)(1),
(2) Date: Apr. 13, 2015

(87) PCT Pub. No.: WO2014/081686
PCT Pub. Date: May 30, 2014

(65) Prior Publication Data
US 2015/0265223 A1     Sep. 24, 2015

Related U.S. Application Data

(60) Provisional application No. 61/728,401, filed on Nov. 20, 2012.

(51) Int. Cl.
*A61B 6/03*     (2006.01)
*A61B 6/12*     (2006.01)
(Continued)

(52) U.S. Cl.
CPC ............ *A61B 6/025* (2013.01); *A61B 6/4405* (2013.01); *A61B 6/5205* (2013.01); *G06T 11/005* (2013.01)

(58) Field of Classification Search
CPC ........... A61B 6/032; A61B 6/026; A61B 6/03; A61B 6/12; A61B 6/14; A61B 6/5258; A61B 6/587; G06T 15/08
(Continued)

(56) References Cited

U.S. PATENT DOCUMENTS

| | | | |
|---|---|---|---|
| 6,609,826 B1 * | 8/2003 | Fujii | A61B 6/12 378/197 |
| 7,016,467 B2 * | 3/2006 | Brooks | A61B 6/563 378/102 |

(Continued)

FOREIGN PATENT DOCUMENTS

EP     2 407 110     1/2012

OTHER PUBLICATIONS

International Search Report, dated Mar. 3, 2014 International Application No. PCT/US2013/070686, 3 pages.

*Primary Examiner* — David A Vanore

(57) ABSTRACT

A mobile radiography apparatus has a moveable (e.g., wheeled) transport frame and an adjustable column mounted at the frame. A boom apparatus supported by the adjustable column can support an x-ray source assembly. Certain exemplary methods and/or apparatus embodiments can provide mobile radiography carts a capability to direct x-ray radiation towards a subject from one or a plurality of different source positions, and reconstruct two-dimensional or three-dimensional tomosynthesis images where an imaging geometry of x-ray source positions to a radiographic detection array is not known for a plurality of x-ray tomosynthesis projection images. In one embodiment, an imaging geometry and tomosynthesis reconstruction(s) can be simul- (Continued)

taneously determined by iteratively determining a current imaging geometry while iteratively monitoring a metric (e.g., stopping criterion) that approaches a prescribed or desired value associated with the tomosynthesis reconstruction.

17 Claims, 20 Drawing Sheets

(51) Int. Cl.
  *G06T 15/08* (2011.01)
  *A61B 6/02* (2006.01)
  *A61B 6/00* (2006.01)
  *G06T 11/00* (2006.01)

(58) Field of Classification Search
  USPC .......... 378/198, 4, 102, 12, 197, 205, 39, 9; 382/128
  See application file for complete search history.

(56) References Cited

U.S. PATENT DOCUMENTS

| | | | | |
|---|---|---|---|---|
| 7,773,791 B2* | 8/2010 | Simon | ............... | G06T 7/0012 382/128 |
| 8,670,521 B2* | 3/2014 | Bothorel | ............... | A61B 6/14 378/205 |
| 2007/0122020 A1 | 5/2007 | Claus et al. | | |
| 2008/0186311 A1 | 8/2008 | Claus | | |
| 2009/0279754 A1* | 11/2009 | Gindele | ............... | G06T 7/0081 382/128 |
| 2014/0369459 A1* | 12/2014 | Foos | ............... | A61B 6/03 378/9 |
| 2015/0250431 A1* | 9/2015 | Yorkston | ............... | A61B 6/548 378/12 |
| 2015/0347682 A1* | 12/2015 | Chen | ............... | G06F 19/321 705/2 |
| 2016/0007946 A1* | 1/2016 | Kleinszig | ............... | A61B 6/5205 378/4 |

* cited by examiner

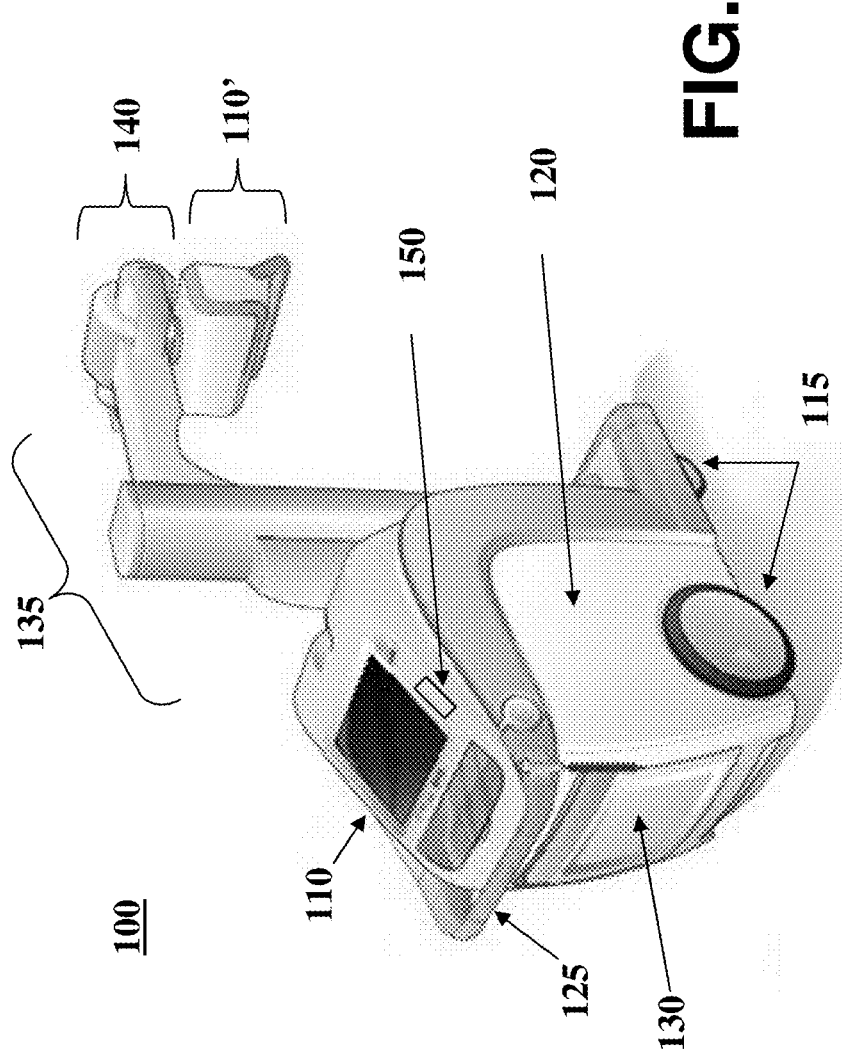

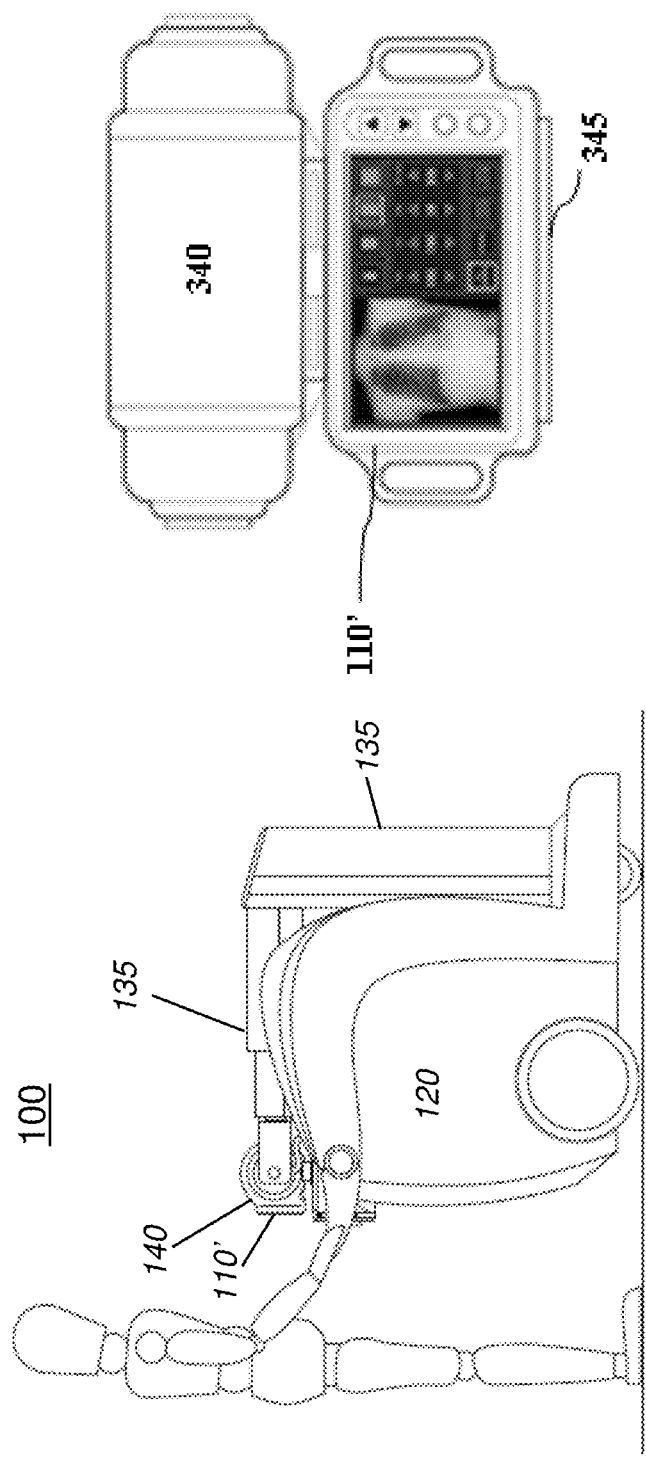

FIG. 5  
110, 110'

| Patient Name | Location | Exam | Exam Time |
|---|---|---|---|
| James Johnson | Rm 203 | Portable Chest | 4/11/2010 11:23:51 AM |
| Fred Smith | Rm 224 | Knee | 4/11/2010 11:24:12 AM |
| Fred Jones | Rm 245 | Portable Chest | 4/11/2010 11:23:44 AM |
| Scott Smith | Rm 252 | Portable Hip | 4/11/2010 11:24:05 AM |
| John Jones | Rm 483 | Portable Hip | 4/11/2010 11:22:48 AM |
| Bill Miller | Rm 508 | Portable Hip | 4/11/2010 11:23:37 AM |
| Bill Smith | Rm 572 | Knee | 4/11/2010 11:23:30 AM |
| Bill Miller | Rm 778 | Portable Chest | 4/11/2010 11:23:16 AM |
| Mike Jones | Rm 884 | Knee | 4/11/2010 11:23:23 AM |
| Robert Jones | Rm 944 | Portable Hip | 4/11/2010 11:23:02 AM |
| Fred Johnson | Rm 993 | Knee | 4/11/2010 11:23:58 AM |

FIG. 6  
110, 110'

New Exam Requested

Routine  Exam Time: 4/11/2010 11:25:01 AM

Location: Rm 816

Patient Name: Mark Bailey

Exam: Portable Hip

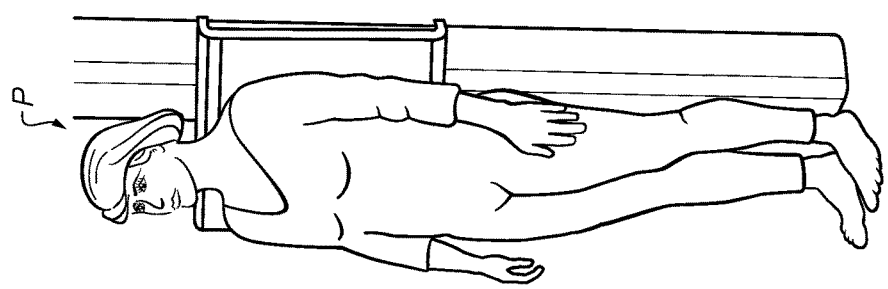
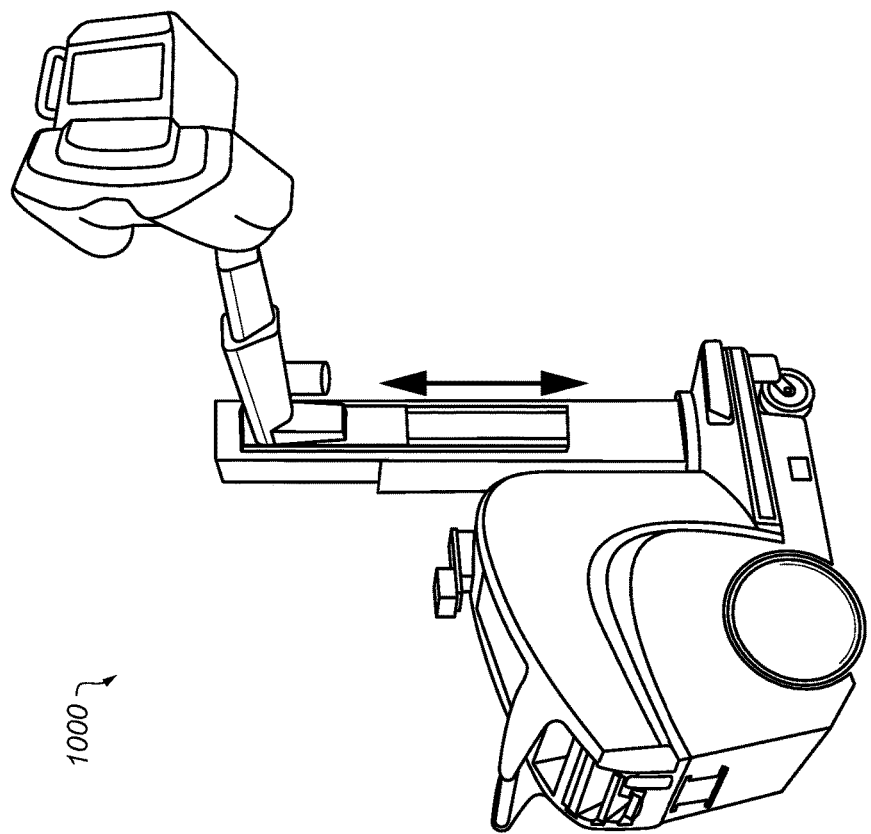
FIG. 11B

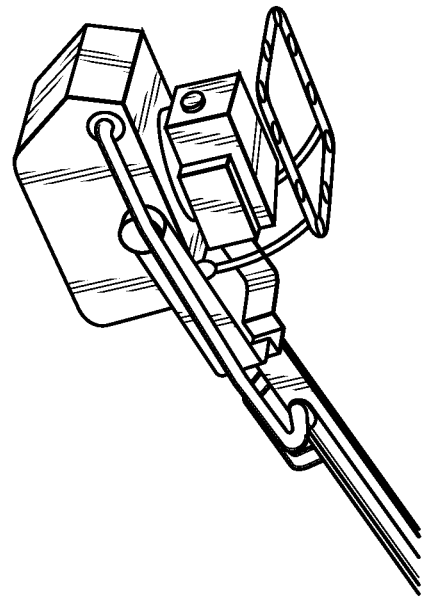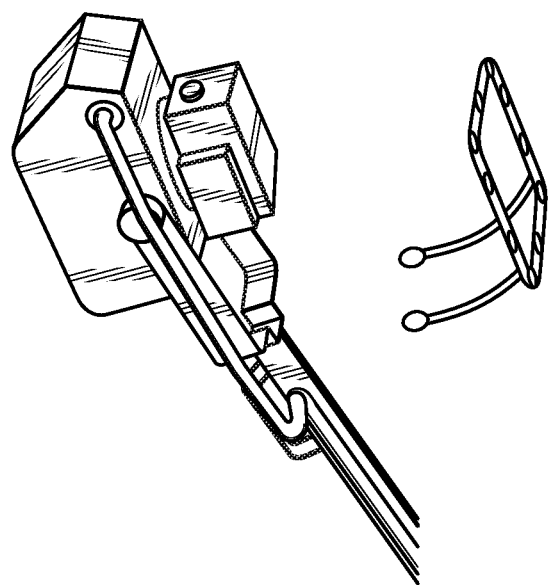
FIG. 19

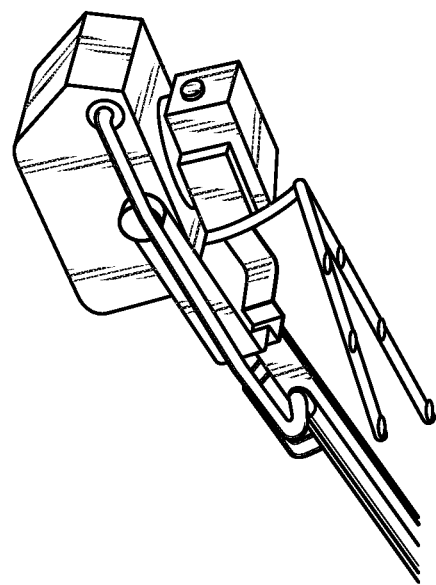
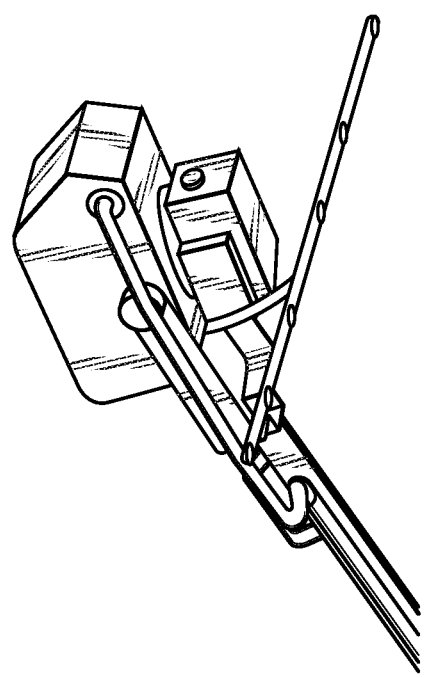
FIG. 20

SCAN GEOMETRY CORRECTIONS FOR TOMOSYNTHESIS MOBILE RADIOGRAPHIC APPARATUS

CROSS REFERENCE TO RELATED APPLICATIONS

This application is a 371 national stage application of earlier filed international application Serial No. PCT/US2013/070686, filed on Nov. 19, 2013 entitled "SCAN GEOMETRY CORRECTIONS FOR TOMOSYNTHESIS MOBILE RADIOGRAPHIC APPARATUS", in the names of Simon et al., which itself claims the benefit of earlier filed Provisional Application Ser. No. 61/728,401, filed on Nov. 20, 2012, entitled "ACQUISITION SCAN GEOMETRY CORRECTIONS FOR TOMOSYNTHESIS APPARATUS AND METHODS FOR MOBILE RADIOGRAPHIC APPARATUS", in the names of Simon et al., all of which are incorporated herein by reference in their entirety.

FIELD OF THE INVENTION

The invention relates generally to the field of medical imaging, and in particular to radiographic imaging apparatus. More specifically, the invention relates to a mobile radiography apparatus having additional tomosynthesis capability.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the orientations of the x-ray tube, patient and detector. This is usually accomplished by either moving both the detector and x-ray source or by fixing the position of the detector (source) and moving the x-ray source (detector). In applications where the detector is fixed, multiple spatially distributed X-ray sources may be used or movable sources may be displaced in various patterns or trajectories. Three-dimensional data is reconstructed from the captured projections in the form of a number of slices through the patient anatomy, each parallel to the detector plane. A consequence of limited angular scanning is that the in depth resolution is much lower than the in-plane resolution of the reconstructed object.

SUMMARY OF THE INVENTION

An aspect of this application is to advance the art of radiography tomosynthesis systems.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which mobile radiography carts can additionally include tomosynthesis capabilities.

Another aspect of the application is to provide methods and/or apparatus embodiments by which mobile radiography carts can acquire projections images and generate the reconstruction of three-dimensional tomosynthesis images.

Another aspect of the application is to provide methods and/or apparatus embodiments by which mobile radiography carts can acquire x-ray tomosynthesis projection images and generate the reconstruction of two-dimensional or three-dimensional tomosynthesis images where an imaging geometry of x-ray source positions to a radiographic detection array is not known for the plurality of x-ray tomosynthesis projection images.

Another aspect of the application is to provide methods and/or apparatus embodiments by which mobile radiography carts can acquire projections images, and then an imaging geometry and tomosynthesis reconstruction(s) can be simultaneously determined by iteratively determining an imaging geometry while iteratively monitoring a metric (e.g., stopping criterion) that approaches a prescribed or desired value associated with the tomosynthesis reconstruction.

In accordance with one embodiment, the present invention can provide a method for digital radiographic 3D tomographic image reconstruction, executed at least in part on a computer, that can include obtaining image data for a plurality of 2D tomographic projection images over a range of scan angles; generating a three-dimensional reconstruction using the plurality of 2D tomographic projection images and a first imaging geometry for the plurality of 2D tomographic projection images; determining a tomographic reconstruction performance metric for a current three-dimensional reconstruction; comparing the tomographic reconstruction performance metric to a prescribed value; and setting the first imaging geometry to an adjusted imaging geometry and repeating the generating through setting operations when the tomographic reconstruction performance metric is not equivalent to the prescribed value, otherwise storing the current three-dimensional reconstruction and first imaging geometry in a computer-accessible memory.

In accordance with one embodiment, the present invention can provide a radiography apparatus that can include a moveable transport frame; a handle; an adjustable support structure coupled to the moveable transport frame; an x-ray source assembly mounted to the adjustable support structure configured to direct x-ray radiation towards a subject from a plurality of different source positions; control circuitry at the mobile x-ray radiography apparatus and coupled to the X-ray source assembly, the control circuitry configured to receive projection image data sets for the plurality of different source positions for reconstruction of tomosynthesis images.

In accordance with one embodiment, the present invention can provide a method for use in a mobile x-ray radiography apparatus that can include obtaining a plurality of x-ray tomosynthesis projection images of an object; and generating a three-dimensional reconstruction of the object using the x-ray projection images; where an imaging geometry of a plurality of x-ray source positions relative to a radiographic detection array is not known for the plurality of x-ray tomosynthesis projection images.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of exemplary embodiments of the invention, as illustrated in the accompanying drawings.

The elements of the drawings are not necessarily to scale relative to each other.

FIG. 1 is a diagram that shows a perspective view of a mobile radiography unit that can use portable radiographic detectors or flat panel detectors according to embodiments of the application.

FIG. 2 is a diagram that shows a perspective view of a mobile radiography unit of FIG. 1 positioned for travel.

FIG. 3 is a diagram that shows an exemplary embodiment of a display/monitor as a second display mounted to a boom assembly of a mobile radiography unit according to the application.

FIGS. 5-8 are diagrams that illustrate exemplary functions implemented at embodiments of a mobile x-ray imaging apparatus.

FIGS. 11A-11B are diagrams that show perspective views of alternative mobile radiography units that can provide a tomosynthesis capability according to embodiments of the application.

FIGS. 19-20 are diagram that show mobile radiographic imaging systems that can include first and second (e.g., multiple) radiographic x-ray sources according to embodiments of the application.

DESCRIPTION OF EXEMPLARY EMBODIMENTS

Figure 4:
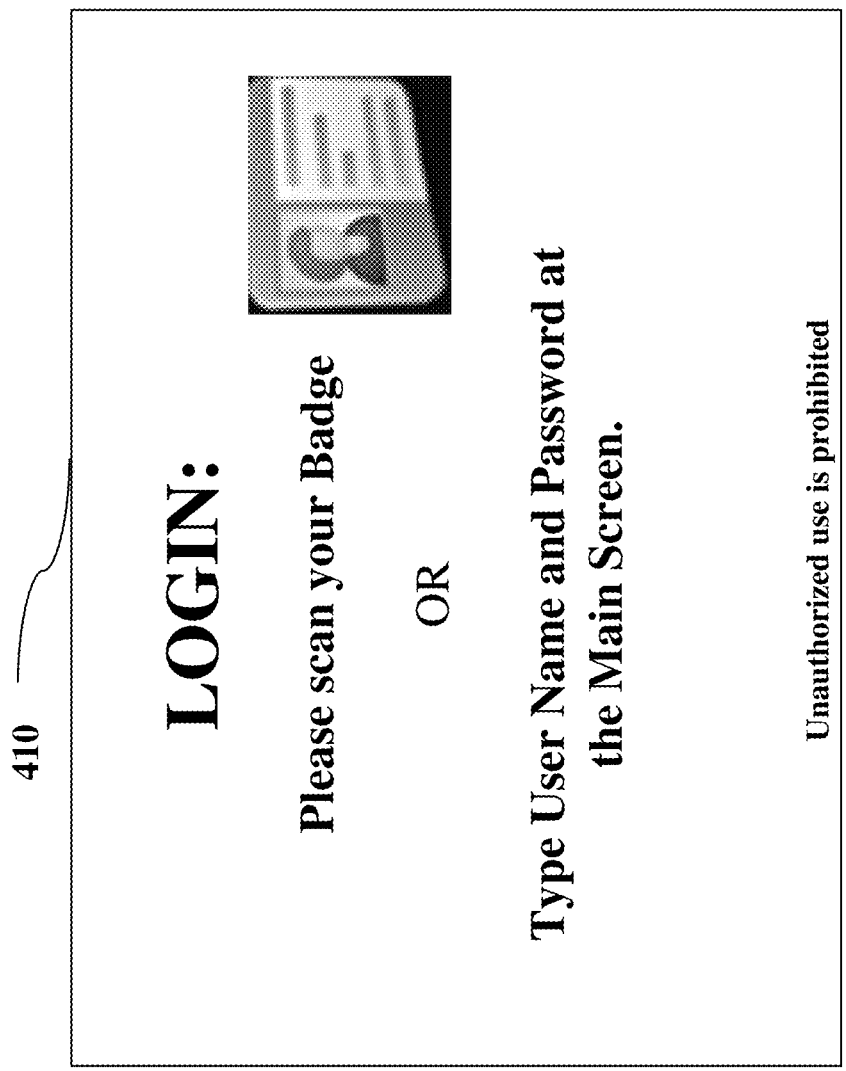
FIG. 4 is a diagram that illustrates an embodiment of a sign on screen according to the application.

Portable radiographic systems are routinely used in hospitals. Compared to standard projection radiography, tomosynthesis provides improved depiction of fine details not visible in normal radiographs due to overlying structures. These benefits provide the impetus to develop portable tomosynthesis systems that can be utilized in the intensive care unit, emergency department, and operating rooms where moving patient is either impracticable or ill advised due to the risk of doing further damage to the patient.

The image quality of the reconstruction depends upon the accurate knowledge of the acquisition scan geometry, the position of the x-ray source and detector for each projection. Uncertainties in the scan geometry can lead to artifacts and/or blurring in the reconstructed object. The development of portable tomosynthesis systems have been hampered by the difficulties in accurately determining the acquisition scan geometry. There remains a need for improved X-ray tomosynthesis systems that can be made portable and still provide reliable clinical images and data.

The following is a description of exemplary embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

FIG. 1 is a diagram that shows a perspective view of a mobile radiography unit that can use portable radiographic detectors or flat panel detectors according to embodiments of the application. The exemplary mobile x-ray or radiographic apparatus of FIG. 1 can be employed for digital radiography (DR) and/or tomosynthesis. As shown in FIG. 1, a mobile radiography apparatus 100 can include a moveable transport frame 120 that includes a first display 110 and an optional second display 110' to display relevant information such as obtained images and related data. As shown in FIG. 1, the second display 110' can be pivotable mounted at the x-ray source 140 to be viewable/touchable from a 360 degree area.

The displays 110, 110' can implement or control (e.g., touch screens) functions such as generating, storing, transmitting, modifying, and printing of an obtained image(s) and can include an integral or separate control panel (not shown) to assist in implementing functions such as generating, storing, transmitting, modifying, and printing of an obtained image(s).

For mobility, the mobile radiographic apparatus 100 can have one or more wheels 115 and one or more handle grips 125, typically provided at waist-level, arm-level, or hand-level, that help to guide the mobile radiographic apparatus 100 to its intended location. A self-contained battery pack (e.g., rechargeable) can provide source power, which can reduce or eliminate the need for operation near a power outlet. Further, the self-contained battery pack can provide for motorized transport.

For storage, the mobile radiographic apparatus 100 can include an area/holder for holding/storing one or more digital radiographic (DR) detectors or computed radiography cassettes. The area/holder can be storage area 130 (e.g., disposed on the frame 120) configured to removably retain at least one digital radiography (DR) detector. The storage area 130 can be configured to hold a plurality of detectors and can also be configured to hold one size or multiple sizes of DR detectors.

Mounted to frame 120 is a support column 135 that supports an x-ray source 140, also called an x-ray tube, tube head, or generator that can be mounted to the support member 135. In the embodiment shown in FIG. 1, the support member (e.g., column 135) can include a second section that extends outward a fixed/variable distance from a first section where the second section is configured to ride vertically up and down the first section to the desired height for obtaining the image. In addition, the support column is rotatably attached to the moveable frame 120. In another embodiment, the tube head or x-ray source 140 can be rotatably coupled to the support column 135. In another exemplary embodiment, an articulated member of the support column that bends at a joint mechanism can allow movement of the x-ray source 140 over a range of vertical and horizontal positions. Height settings for the x-ray source 140 can range from low height for imaging feet and lower extremities to shoulder height and above for imaging the upper body portions of patients in various positions.

As shown in FIG. 2, for ease during transport of the mobile radiographic apparatus 100, the support member 135 and x-ray source 140 can be arranged close to frame 120. As shown in FIG. 2, the second display 110' can be in a viewable position (e.g., operable) during transport of the mobile radiographic apparatus 100. When the mobile radiographic apparatus 100 is to be used, the support member 135 and x-ray source 140 can be extended from the frame 120 for proper positioning (e.g., by the operator, a user, or x-ray technician) and the second display 110' moved to viewable position such as shown in FIG. 1.

FIG. 3 is a diagram that shows an exemplary embodiment of a display/monitor as a second display mounted to a boom assembly of a mobile radiography unit according to the application. As shown in FIG. 3, the second display 110' can be mounted to a collimator 345 of an x-ray source 340 of a support member 135 of a mobile radiography unit. In one embodiment, the collimator 345 can be rotably mounted to the x-ray source 340 so that the collimator 345 (e.g., second display 110') can swivel at least 90 degrees, at least 180 degrees or 360 degrees. As shown in FIG. 3, the second display 110' is coupled to a plurality of handles for ease of positioning. Alternatively, the second display 110' can be mounted to (e.g., rotatably) an x-ray source 340 above a collimator 345 of a boom assembly of a mobile radiography unit.

FIG. 4 is a diagram that illustrates an embodiment of a sign on screen according to the application. Thus, when an attempt is made to operate the mobile x-ray imaging apparatus 100, a sign on screen 410 can be displayed to provide instructions to a user. As shown in FIG. 4, the single sign on screen 410 can provide instructions for sign on sign on and activate the mobile x-ray system 100 such as "LOGIN: Please scan your badge or type User Name and Password at the main screen." Exemplary embodiments of a pass key or ID badge can include but are not intended to be limited to a card reader such as a smart card, a magnetic stripe card, bar code data, or a proximity reader compatible with access technologies such as RFID, bluetooth, wireless communication device, a proximity card, a wireless smart card, a wiegand card, a magnetic reader device/card, an optical reader device/card, an infrared reader device/card, or biometric data such as fingerprints, eye scan or the like.

According to exemplary embodiments of the application, the first display 110 and the second display 110' can provide information such as but not limited to: (i) general information such as date, time, environment conditions, and the like; (ii) unit information such as model serial number, operating instructions, warning information, and the like; (iii) patient data, such as patient name, room number, age, blood type, and the like; (iv) indicators such as but not limited to cart power/battery indicators, detector status (e.g., on/off), wireless signal strength/connectivity, grid alignment aides, cart diagnostics and/or (v) imaging/procedure information, such as the exam type, exposure information, and the like.

According to embodiments of the application, the first display 110 and the second display 110' can provide capabilities/functionality to the mobile x-ray imaging apparatus 100 such as but not limited to: (i) view and/or change x-ray exposure parameters, tube/generator/technique settings; (ii) view and/or change image information, such as a list of views (e.g., body part & projection) to perform for the patient, relevant information about those views, the ability to select a view to perform, and an x-ray image of an acquired view; (iii) display and/or change patient information, such as: Patient Name, Room number, Patient ID, date of birth (e.g., to confirm that the correct patient); (iv) display and/or change a Patient Worklist, such as a list of exams to perform and allow the user to select an exam. (In one embodiment, such a patient worklist can be automatically updated (e.g., synchronized to a master/hospital/doctor worklist) using a wired or wireless network/connection. In one embodiment, the mobile x-ray imaging apparatus 100 can highlight/indicate new exams (e.g., on the second display 110') upon receipt of the scheduled examination.); (v) display generator/source current values and controls to change those values, such as: kVp, mA, mAs, Time, ECF, focal spot, collimator, filter, AEC, grid; (vi) display detector selection and allow the technician to select/activate a different detector; (vii) display recently acquired images and allow editing of those images, exemplary acquired (e.g., recently) or previous images can be displayed full size, partial size or with corresponding image information; (viii) display previously acquired images (e.g., related prior images of a patient) and allow editing of those images; or (ix) display a video of what is in front of the mobile x-ray imaging apparatus 100 during transport, e.g., using a video camera located on the other side (e.g., front side of the mobile x-ray imaging apparatus 100). In one embodiment, the mobile x-ray system 100 can include a collision avoidance system with alerts (e.g., audible, visual), and automatic maneuvering to avoid contact in the examining room (e.g., by stopping or course modification).

Figure 7:
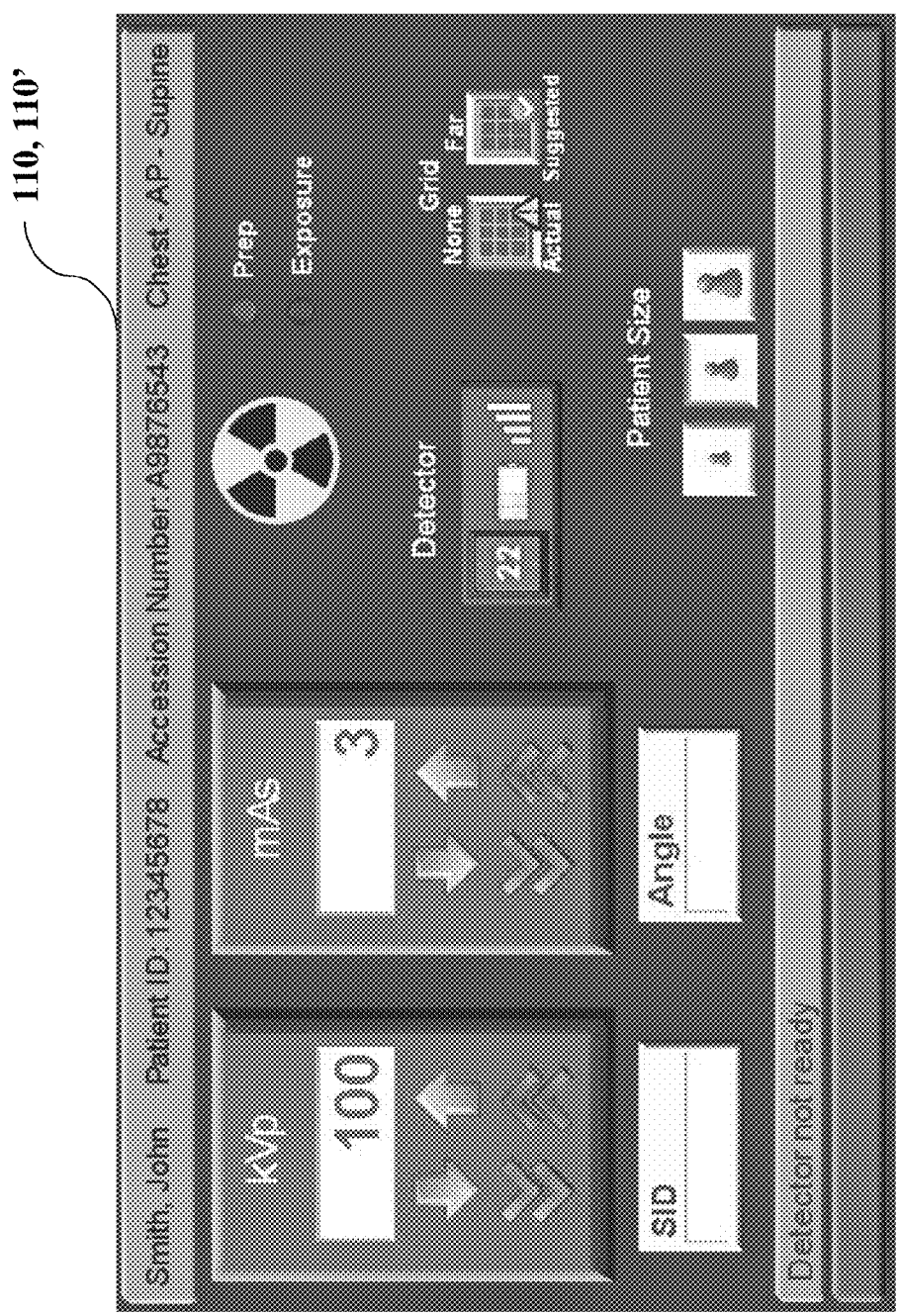
Figure 8:
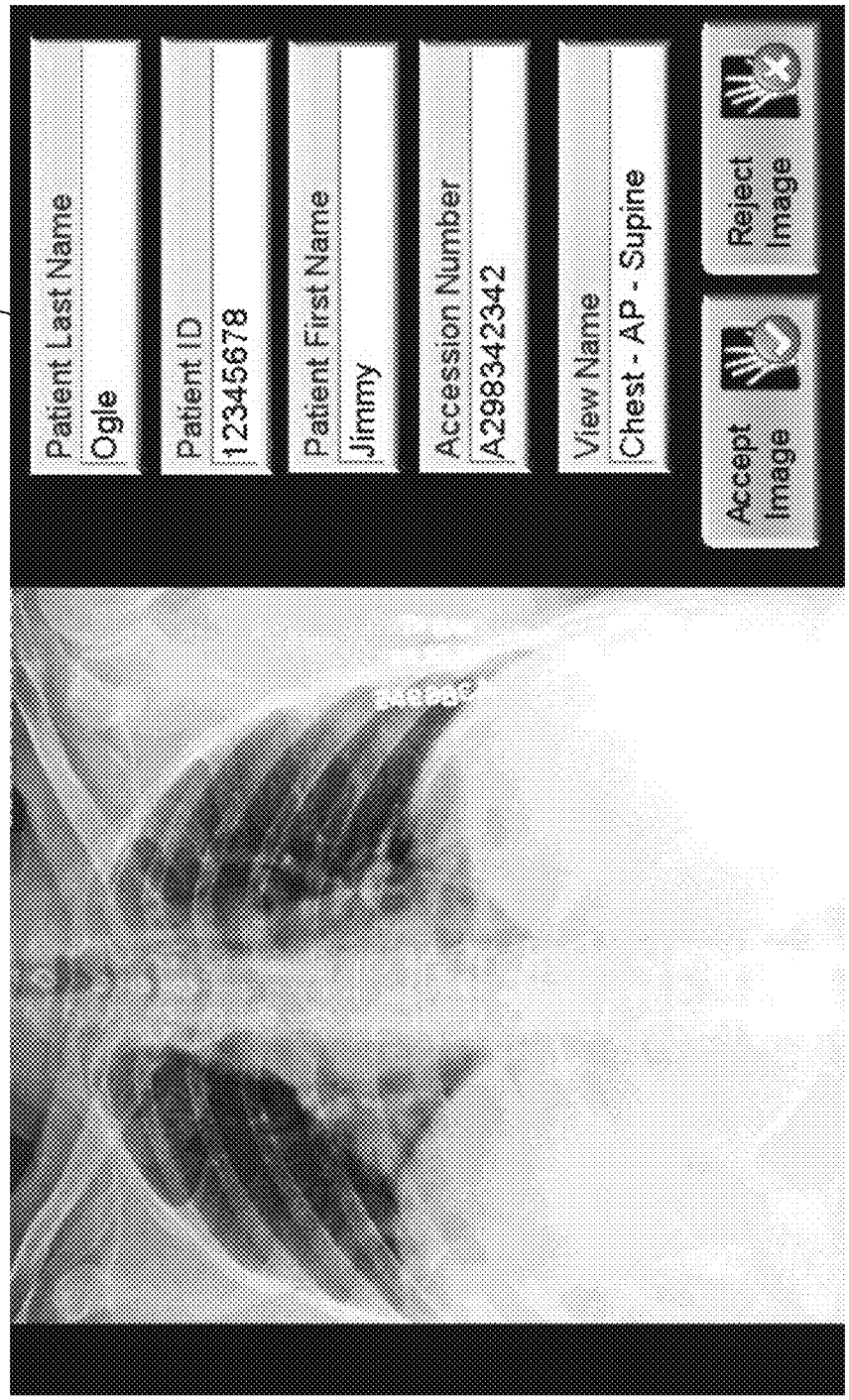

FIGS. 5-8 are diagrams that illustrate exemplary non-limiting representative functions illustrated on an embodiment of a second display of a mobile x-ray imaging apparatus. As shown in FIG. 5, an example of a work list is shown on a monitor of the second display 110'. As shown in FIG. 6, an example of a new examination/procedure information/requirement for that technician and/or patient is shown on a monitor of the second display 110'. As shown in FIG. 7, an example of x-ray source controls is shown on a monitor of the second display 110'. As shown in FIG. 8, an example of newly acquired image and patient information is shown on a monitor of the second display 110'.

In one embodiment, the mobile radiographic imaging apparatus can be operated/controlled by programmed control logic in the first or second displays. For example, the programmed control logic can include a processor and display, an integrated computer system, or a portable computer and applications to operate thereon.

Figure 9:
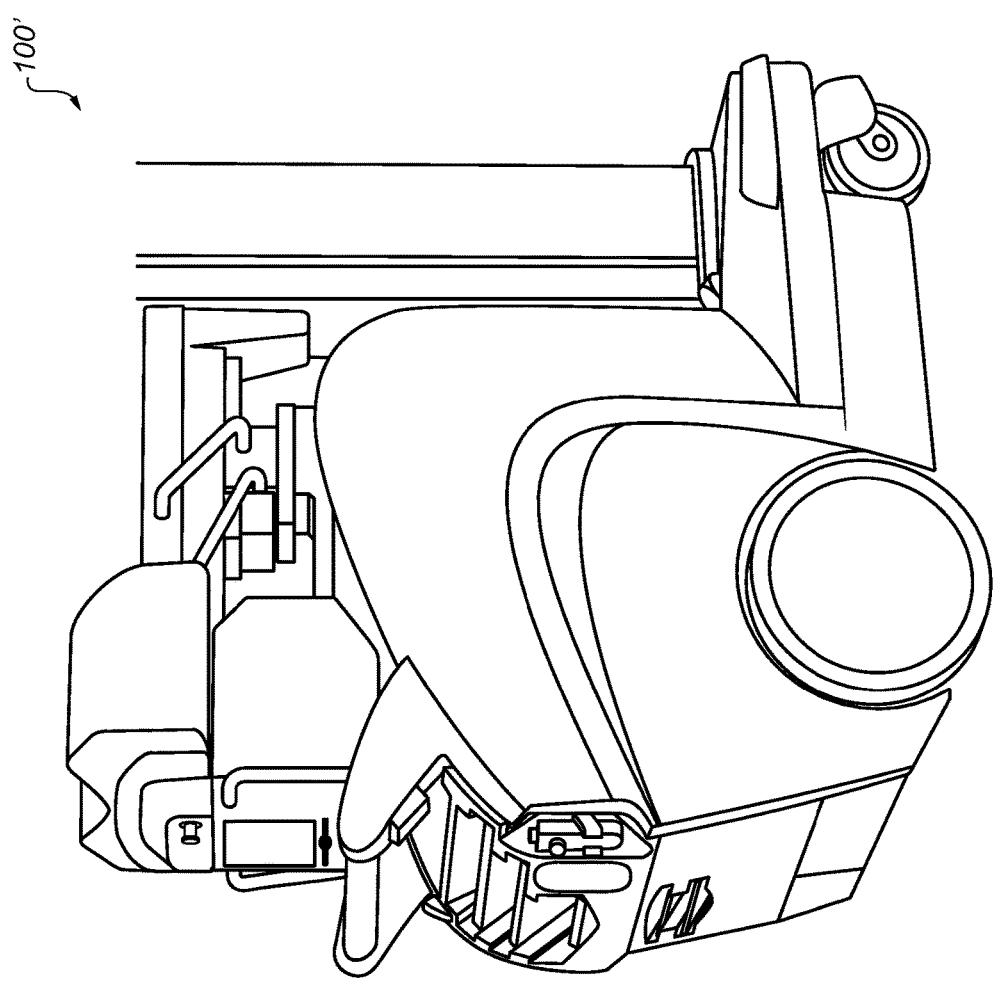
FIG. 9 is a diagram that shows a perspective view of a mobile radiography unit according to another embodiment of the application.

FIG. 9 is a diagram that shows a perspective view of a mobile radiography unit according to another embodiment of the application.

Figure 10:
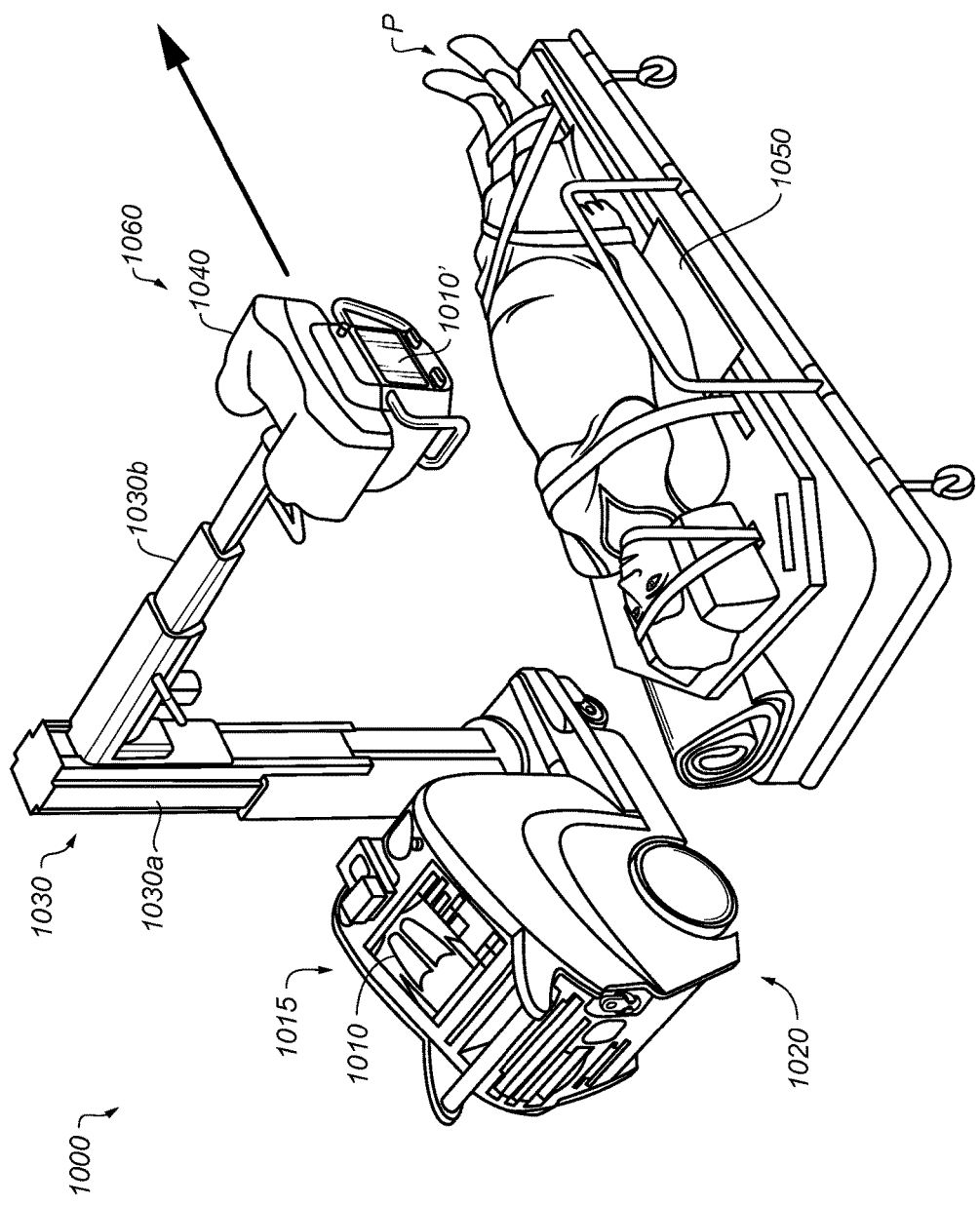
FIG. 10 is a diagram that shows a perspective view of a mobile radiography unit that can provide a tomosynthesis capability according to embodiments of the application.

FIG. 10 is a diagram that shows a perspective view of a mobile radiography unit that can provide a tomosynthesis capability according to embodiments of the application. In one embodiment, a mobile radiography unit that be a tomosynthesis system. As shown in FIG. 10, an embodiment of a portable tomosynthesis system 1000 is shown that can include a movable transport frame 1020. Mounted to the moveable transport frame 1020 can be a support column that supports an x-ray source 1040. As shown in FIG. 10, a support column 1030 can include a second section 1030b that extends outward a fixed/variable distance from a first section 1030a where the second section 1030b is configured to ride vertically up and down the first section 1030a to the desired height for obtaining the projection images. The system also includes a digital x-ray detector 1050 that is wirelessly connected to a system controller 1015 contained inside the moveable transport frame 1020. The system controller 1015 can implement and/or control the functionality of the mobile radiographic unit 1000 (e.g., functionality provided through the displays 100, 100'). The system controller 1015 can be provided though one or more of a conventional general purpose processor, digital computer, microprocessor, RISC processor, signal processor, CPU, arithmetic logic unit (ALU), video digital signal processor (VDSP) and/or similar computational machines, programmed according to the teachings of the application, as will be apparent to those skilled in the relevant art(s). The x-ray source 1040 can use a collimator to form beams that are directed towards the detector 1050. The x-ray source 1040 may also include positioning, such as motors, which allow for directing the beam towards the detector. The moveable transport frame 1020 can include a first display 1010 and the x-ray source 1040 can be coupled to a second optional display 1010'. The system controller 1015 can coordinate operations of the x-ray source 1040, detector 1050, and moveable transport frame 1020. The system controller 1015 can control operations of the x-ray source, which may include the collimator, positioning devices and triggering of image acquisition by emission of x-rays from the source. The system controller 1015 also can control operations of the detector 1050, which may include triggering of the image acquisition and transmission of the acquired images back to the controller. In addition, the system controller 1015 can control the movement of the transport frame 1020. FIG. 10 shows an embodiment of a portable tomosynthesis system where the x-ray source 1040 assembly can be moved along a prescribed path relative to the detector 1050 or relative to geometry of the detector 1050 and/or a patient (object) to be imaged. As shown in FIG. 10, the moveable transport frame 1020 can move the x-ray source 1040 assembly along a prescribed path (e.g., linear/non-linear motion) illustrated by an arrow.

Figure 11A:
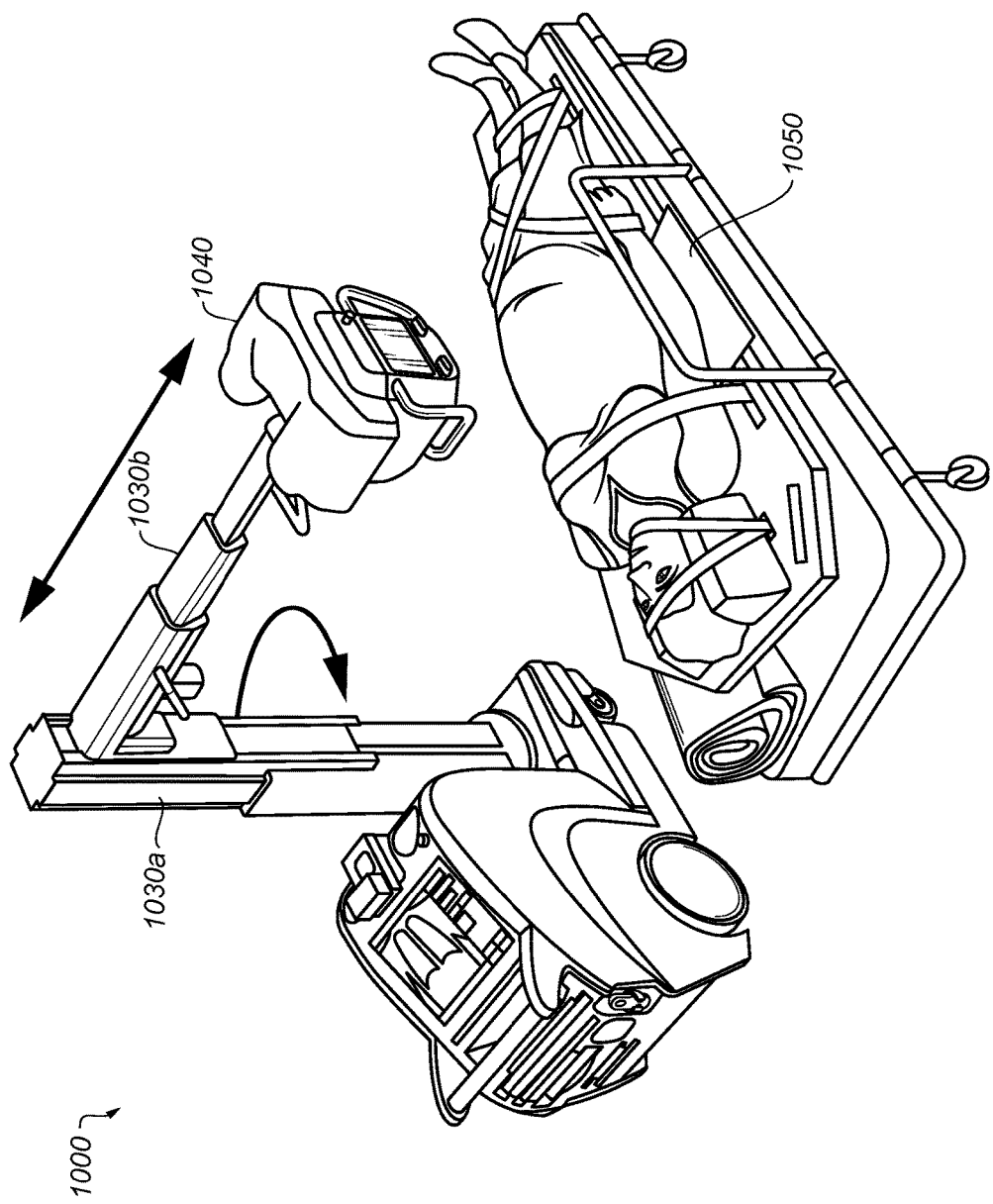

FIGS. 11A-11B are diagrams that show perspective views of additional mobile radiography units that can provide tomosynthesis capabilities according to embodiments of the application. As shown in FIG. 11A, the support column 1030 can move the x-ray source 1040 assembly along a prescribed path (e.g., linear/non-linear, curved, 2D or 3D) illustrated by an arrows. In certain exemplary embodiments, the second section 1030b and/or the first section 1030a can independently move the x-ray source 1040 assembly or move the x-ray source 1040 assembly in combination (e.g., concurrently). Further, the moveable transport frame 1020 can move the x-ray source 1040 assembly in combination with the support column 1030. In one embodiment, the mobile radiography units that can include a tomosynthesis capability as shown in FIG. 11B can further be used for LLI (Long Length Imaging).

Figure 12:
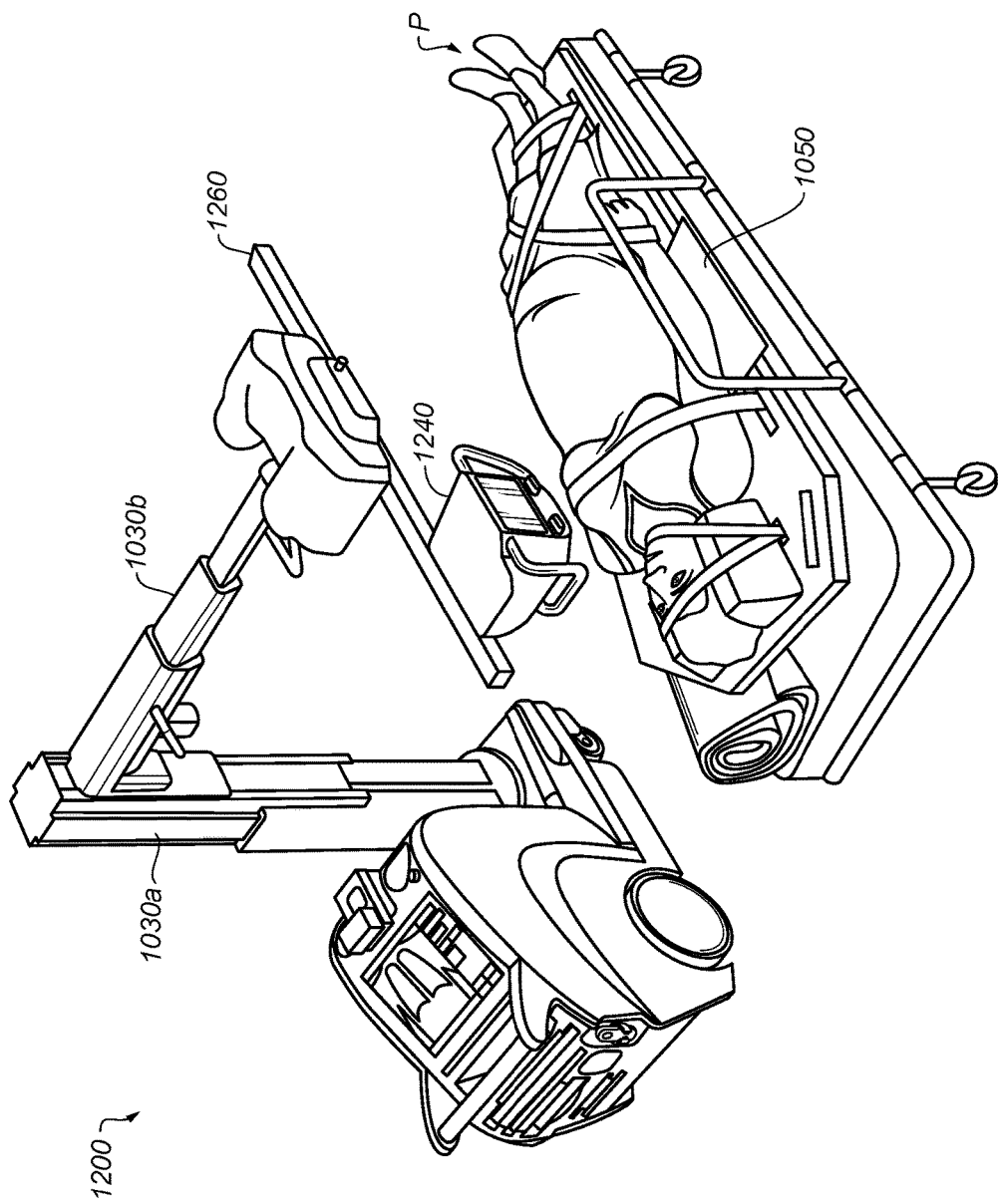
FIG. 12 is a diagram that shows a perspective view of another mobile radiography unit that can provide a tomosynthesis capability according to embodiments of the application.

FIG. 12 is a diagram that shows a perspective view of another mobile radiography unit that can provide a tomosynthesis capability according to embodiments of the application. In one embodiment of a portable tomosynthesis system, an x-ray source assembly can be configured to move along a prescribed path (e.g., linear path). FIG. 12 shows an embodiment of a portable tomosynthesis system where the x-ray source 1040 assembly is replaced by an X-ray source 1240 designed to move along a linear path on a support track 1260.

Figure 13:
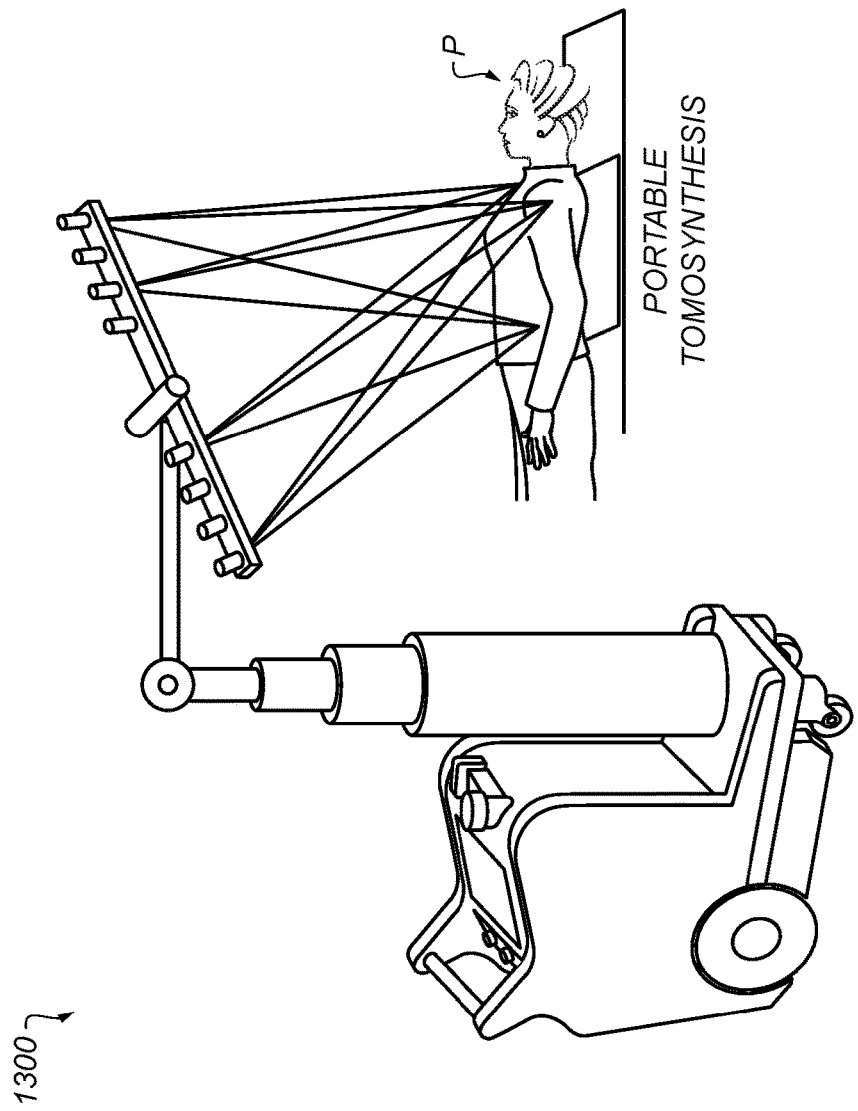
FIG. 13 is a diagram that shows a perspective view of yet another mobile radiography unit that can provide a tomosynthesis capability according to embodiments of the application.

FIG. 13 is a diagram that shows a perspective view of another mobile radiography unit that can provide a tomosynthesis capability according to embodiments of the application. In certain exemplary embodiment of portable tomosynthesis systems, the moveable mounted x-ray source can be replaced by a plurality of multiple individually controlled x-rays sources. FIG. 13 shows an embodiment of a portable tomosynthesis system where the multiple individually controlled x-rays sources are distributed sources (e.g., linearly distributed). The distributed sources can be arrayed in a prescribed spatial relationship.

Figure 17:
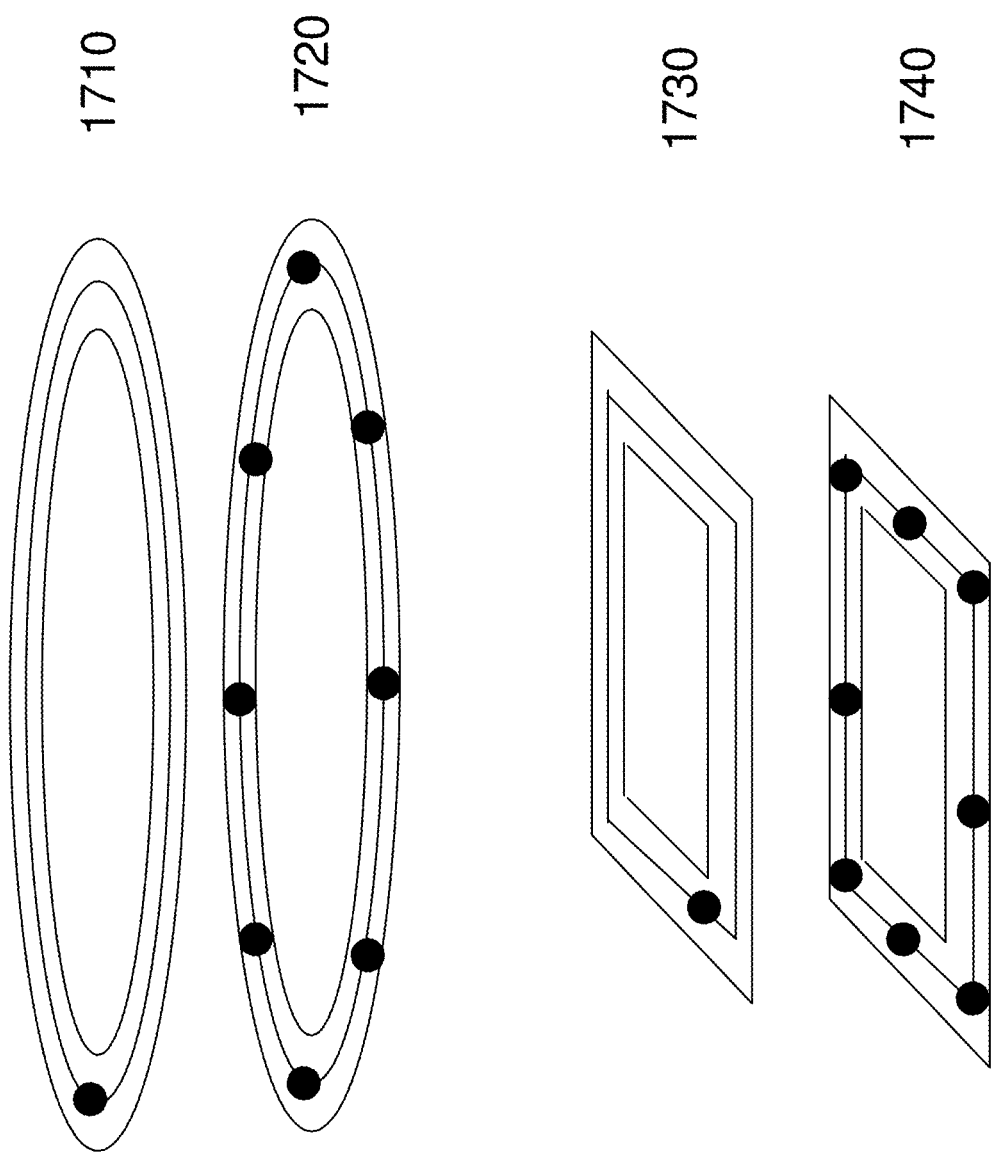
FIG. 17 is a diagram that shows examples of non-linear x-ray scan paths according to embodiments of the application.

Alternatively, different x-ray source paths can be used to modify or address reconstruction artifacts that can be caused by limited angular scanning systems such as radiographic tomosynthesis imaging systems. In addition, various x-ray scan paths can be use to accentuate the desired imaged structures and/or reduce or minimize artifacts that might confound or mask the ability to make an accurate diagnosis. FIG. 17 is a diagram that shows examples of non-linear x-ray scan paths (e.g., circular and square paths). In one embodiment, the moveable x-ray source is mounted on a circular 1710 (square 1730) track or a plurality of sources are spatially distributed in a circular 1720 (square 1740) pattern. However, embodiments of the application are not intended to be so limited, for example other non-linear, curved, 2D or 3D scan paths or movable x-ray supports can be used. Further, source assemblies can be used to ensure that radiation emitted by the moveable or distributed x-ray source is directed towards the detector (e.g., through the object/patient). In one embodiment, the source assemblies can include adjustable collimators (e.g., before or during an image acquisition scan). In one embodiment, the adjustable collimators can be individually and/or concurrently moved.

In one embodiment, a mobile radiographic imaging system is intended to support critically ill patients in an ICU that are currently transported out of ICU for x-ray imaging. For example, ICU patients can receive a tomosysthesis procedure that might otherwise be transported out of ICU in order to obtain a CT exam. For example, CT imaging is often needed for ICU patients in order to differentiate various types of fluids induced by plural effusions, such as blood, water, and the like, so that corrective actions can be taken. However, transporting ICU patients to the CT exam area can be a challenging task due to their severe clinical conditions. Further, visualization software can be provided to facilitate interpretation of ICU-related chest abnormalities. For instance, presentation of the low exposure sequences (prior to reconstruction of the slide data) that allows the ICU physician to "look around" rib structures and the like.

Figure 14A:
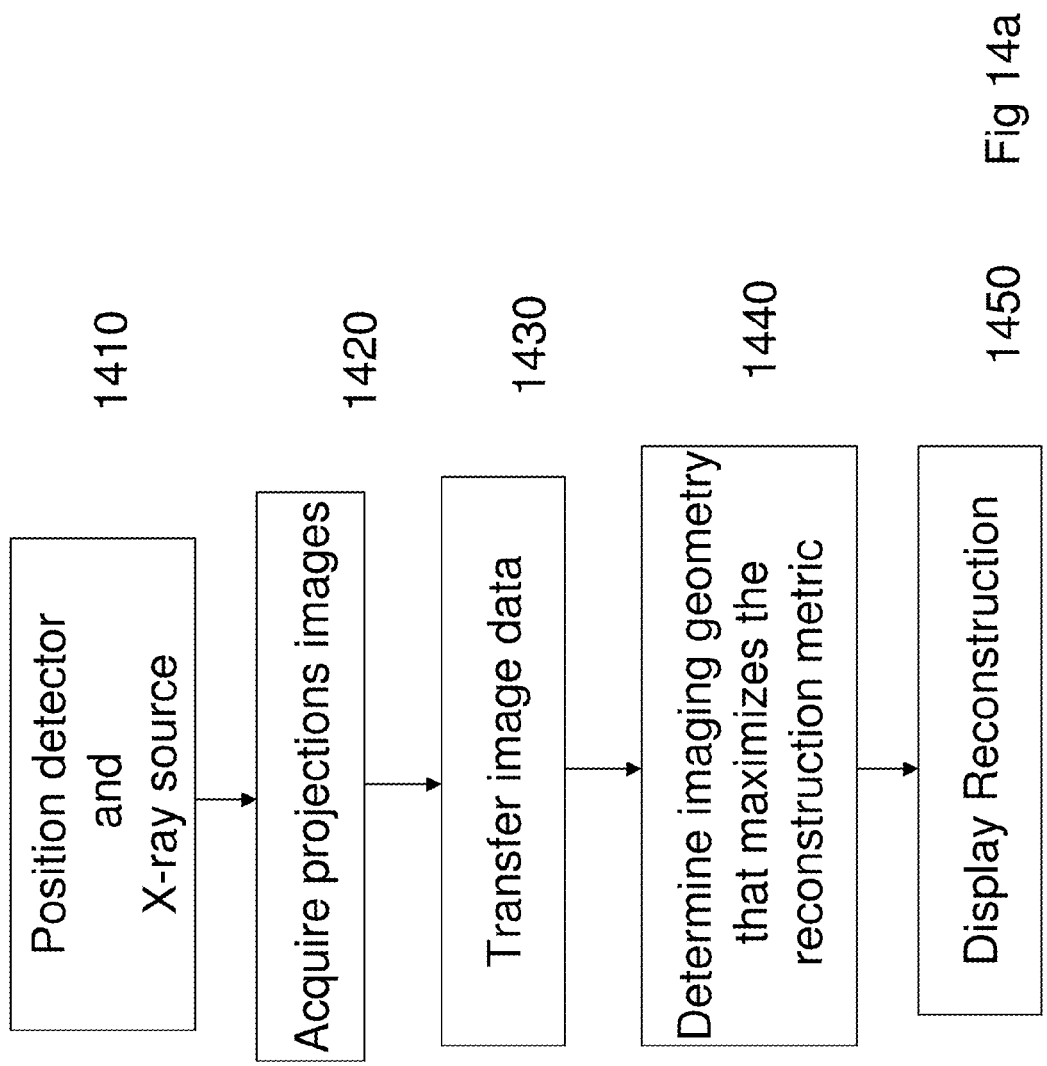
FIG. 14a is a flow chart that shows an exemplary method of operating exemplary mobile radiographic imaging systems for acquiring projections images and generating reconstructions of (e.g., three-dimensional) tomosynthesis images according to embodiments of the application.

Referring to FIG. 14a, a flow chart that shows an exemplary method of acquiring projections images and generating the reconstruction of three-dimensional tomosynthesis images, will now be described. The method for acquiring projections images and generating the reconstruction of three-dimensional tomosynthesis images will be described using embodiments of mobile radiography apparatus shown in FIGS. 10-13 and can be applied to mobile x-ray systems/carts shown in FIGS. 1 and 10-13; however, the method of FIG. 14a is not intended to be limited thereby.

As shown in FIG. 14a, the detector and x-ray source can be positioned (operation block 1410). For example, the x-ray source can be moved to its initial position and the detector can be positioned such that the patient P is interposed between the detector and x-ray source.

For exemplary portable tomosynthesis system embodiments 1000, 1200, 1300, the initial x-ray source assembly position can be set by the location of the transport frame and the support column. The height, extent and rotation positioning of the support column's first section 1030a and the second section 1030 can be used to position the x-ray source assembly to the initial desired location above the patient the patient. Alternatively, the support (e.g., support 1260, track 1710, track 1730) and the location of the transport frame and/or the support column can set the initial x-ray source assembly position.

Then, a series of projections image can be acquired at different x-ray source positions (operation block 1420). In embodiment 1000, the projection images can be acquired while the transport frame, and thus attached x-ray source, is moved along a linear or non-linear path. In embodiment 1000, the projection images can be acquired while the height, extent, and rotation of the support columns first and second section are modulated so that the attached x-ray source, is moved along a linear or non-linear path. In embodiment 1200, the projection images can be acquired while the x-ray source is moved along the support track. In embodiment 1300, the projection images can be acquired while individual x-ray sources are triggered.

Then, the acquired projection image data can be received (e.g., transfer back from the detector to) by control and processing components of the system controller (operation block 1430). The projections images can be displayed on display 110 and/or undergo a quality check (e.g., automated or by the operator) before being further processed.

Then, the imaging geometry and the tomosynthesis reconstruction can be simultaneously determined by iteratively determining an imaging geometry (e.g., for source positions and detector position(s)) while iteratively monitoring a metric that approaches a prescribed or desired value (or change in value) associated with the tomosynthesis reconstruction (operation block 1440). For example, the imaging geometry and the tomosynthesis reconstruction can be simultaneously determined by establishing the imaging geometry that maximizes (or minimizes) a metric associated with the tomosynthesis reconstruction (operation block 1440). There are numerous metrics, such as image quality of the final reconstruction or data fidelity of the reconstruction to the measured projections, which can be used to determine the imaging geometry.

Then, the reconstruction volume can be displayed on display 110, 110' (operation block 1450) and/or undergo a quality check before storing the volume. In one embodiment, the reconstruction volume can be stored after the quality check (e.g., before display thereof).

Examples of image quality metrics are metrics that are associated with edge (high frequency) information of the reconstruction, such as the gradient of the reconstructed object $f(\vec{r})$ $$E_1 = \frac{1}{2} \int_V |\nabla f(\vec{r})|^2 d\vec{r}$$

or the laplacian $$E_2 = \frac{1}{2} \int_V |\nabla^2 f(\vec{r})|^2 d\vec{r}.$$

where $\vec{r}=(x, y, z)$ spatial location and V is the volume or sub volume of the reconstruction.

Another type of image quality metric is associated with the probability distribution function (or normalized histogram) $h(z)$ of the reconstructed object $f(\vec{r})$ such as the power density $$E_3 = \int_z h^2(w) dw$$

or entropy $$E_4 = -\int_z h(w) \log(h(w)) dw$$

where $$h(w) = \frac{1}{V} \int_V K(f(\vec{r}) - w) d\vec{r}$$

is the nonparametric kernel density estimate of the probability distribution function of w, is the unit of reconstruction such as attenuation coefficient or Hounsfield unit, for a given kernel K( ). Typical choices for K( ) are the Dirac delta function and the Gaussian kernel.

An example of a data fidelity metric is $$E_5 = \frac{1}{2} \sum_{i=1}^{nProjs} \|A_i f - p_i\|^2$$

or a regularized version, $$E_6 = R(f) + \frac{1}{2} \sum_{i=1}^{nProjs} \|A_i f - p_i\|^2$$

where $A_i$ is the projection matrix for the ith projection, f and p are vector representation of the reconstruction volume and projection images, and R( ) is a regularizer imposing a prior, such as smoothness, on the reconstruction f. The projection matrices A are a function of the imaging geometry.

The image quality of the reconstruction depends upon the accurate knowledge of the position of the x-ray source and detector for each projection. Uncertainties in the scan geometry can lead to artifacts and/or blurring in the reconstruction. Further, accurate positioning of the detector using a grid can be desirable or fundamental to allow impinging x-ray to pass the grid to reach, in whole or in part, the detector. For a portable stationary detector tomosynthesis system, the scan geometry can correspond to the set x-ray source locations relative to the stationary detector. The position encoders associated with the moveable frame and moveable x-ray source assembly can provide accurate information about the spatial location of the x-ray source in a local coordinate system associated with the x-ray source assembly. For a distributed source assembly, the spatial location of x-ray sources can be fixed in the local coordinate system. For the portable tomosynthesis system, the detector and x-ray source are physically separated from each other, as a consequence the relative orientation and distance between x-ray source assembly and the detector local coordinates systems are not accurately known. In one exemplary embodiment, a detector can be physically separated and tethered to the portable tomosynthesis system, however, such system geometry (e.g., position, orientation etc. of detector, x-ray source(s)) can be unknown.

Figures 15A, 15B:
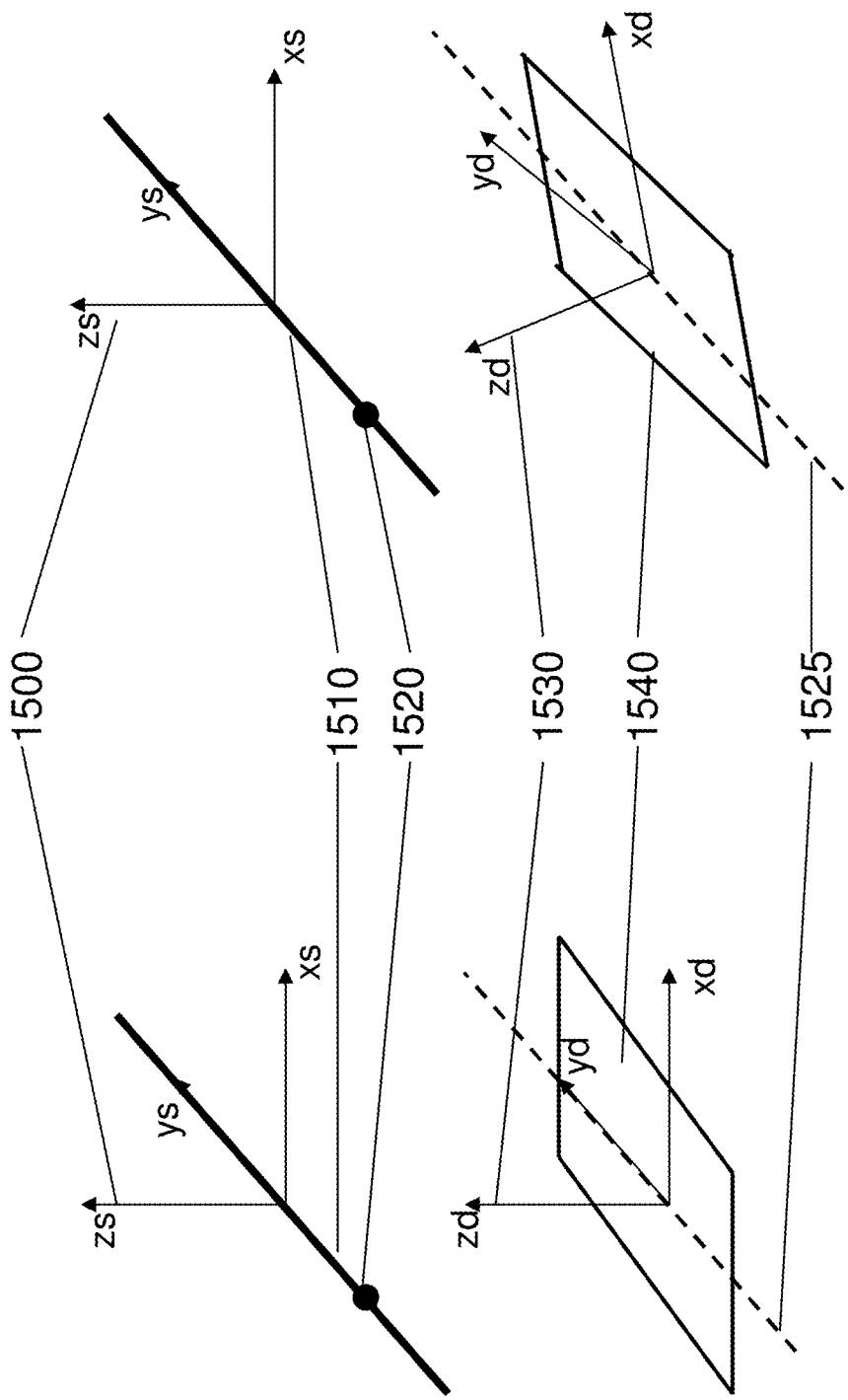
FIG. 15a and FIG. 15b are diagrams that schematically show exemplary relative orientation and distance between an x-ray source coordinate system and an detector coordinate system for a linear scan tomosynthesis system according to embodiments of the application.

FIG. 15a and FIG. 15b are diagrams that schematically show exemplary relative orientation and distance between x-ray source coordinate system 1500 and the detector coordinate system 1530 for a linear scan tomosynthesis system. FIG. 15a shows a desired aligned tomosynthesis system (e.g., selected alignment or ideally aligned), where the detector and x-ray source coordinates have the same orientation. A projection 1525 of the trajectory 1510 of the x-ray source 1520 onto the detector 1540 is aligned with the one of the detector's in plane axes and the distance between the x-ray source and detector is constant along the x-ray source's trajectory. FIG. 15b shows a system where the detector and x-ray source coordinates have different orientations and as a result the distance of the x-ray source to the detector plane now varies along the x-ray source trajectory. As shown in FIG. 12, this type of mismatch in orientation between the x-ray source assembly 1060 and detector 1050 can occur when the detector 1050 is place under a bedridden patient.

Figure 14B:
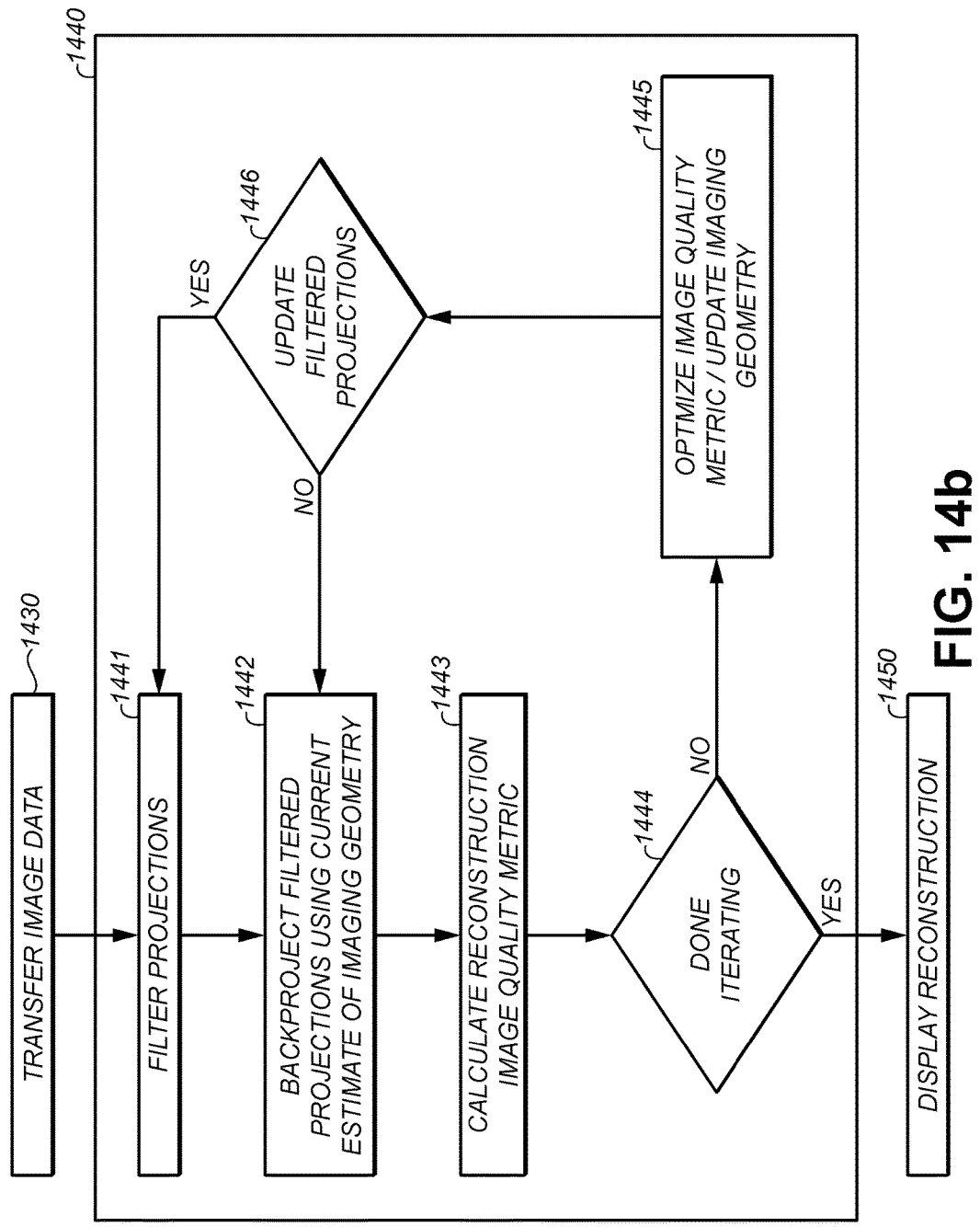
FIG. 14b is a flow chart that shows an exemplary embodiment of a method to determine imaging geometry/reconstructions using image quality metrics associated with a prescribed reconstruction according to embodiments of the application.

FIG. 14b is a flow chart that shows an embodiment of a method to determine the imaging geometry/reconstruction step 1440 using an algorithm that can determine or optimize an image quality metric associated with a filtered backprojection reconstruction algorithm. An algorithm used to accomplish this can be referred to as an imaging geometry auto-correction reconstruction algorithm. In the filter projection operation block 1441, a current estimate of the imaging geometry can be used to generate the filtered projections. In the backproject filtered projections operation block 1442, the filtered projections can be backprojected using the current estimate of the imaging geometry to generate a current reconstruction. In calculate reconstruction image quality metric operation block 1443, an image quality metric such as L2 norm as defined by $E_1$ is calculated for the current reconstruction. In the iterating complete operation block 1444, the optimization can be terminated if a stopping condition for image quality metric has been achieved; otherwise the process (e.g., optimization) continues. Examples of stopping condition can be the image quality metric has converged to maximum (or minimum) value, relative change in the metric is below a given threshold or a maximum number of iterations have been reached.

One feature of the imaging geometry auto-correction reconstruction algorithm can be performed in the optimize image quality metric/update imaging geometry operation block 1445, where the image quality metric is optimized with respect to the imaging geometry. Exemplary optimization procedures can determine updates to the imaging geometry that achieve the desired (e.g., maximize or minimize) the image quality metric. Exemplary optimization procedures of the imaging geometry can be carried out over the whole or subset of the reconstruction. Exemplary subsets can be a set of axial slices or sub volumes of interest that are determined from the initial reconstruction using the assumed imaging parameters.

Some commonly used optimization algorithms are downhill-simplex, Powell's method, and gradient descent methods. For example using a gradient descent method to optimize(maximize) the L2 norm of the reconstruction $E_1$ $$E_1 = \frac{1}{2}\int |\nabla f(\vec{r})|^2 d\vec{r} = \frac{1}{2}\int \nabla f_x^2(\vec{r}) + \nabla f_y^2(\vec{r}) + \nabla f_z^2(\vec{r}) d\vec{r}.$$

The derivative of $E_1$ with respect to the set of imaging parameters $\alpha$ is given by $$\frac{\partial E_1}{\partial \alpha} = \int \nabla f_x(\vec{r}) \frac{\partial \nabla f_x(\vec{r})}{\partial \alpha} + \nabla f_y(\vec{r}) \frac{\partial \nabla f_y(\vec{r})}{\partial \alpha} + \nabla f_z(\vec{r}) \frac{\partial \nabla f_z(\vec{r})}{\partial \alpha} d\vec{r}$$

These derivatives can be determined either analytically or numerically using the filtered backprojection reconstruction algorithm.

The derivatives are then used to update the current estimate $\alpha^k$ to yield a new estimate $\alpha^{k+1}$ is given by $$\alpha^{k+1} = \alpha^k + \delta^k \frac{\partial E_1}{\partial \alpha}$$

where $\delta^k$ is a step size which can either be a constant or an optimal step size can be calculated using a line search for each update.

Figure 16:
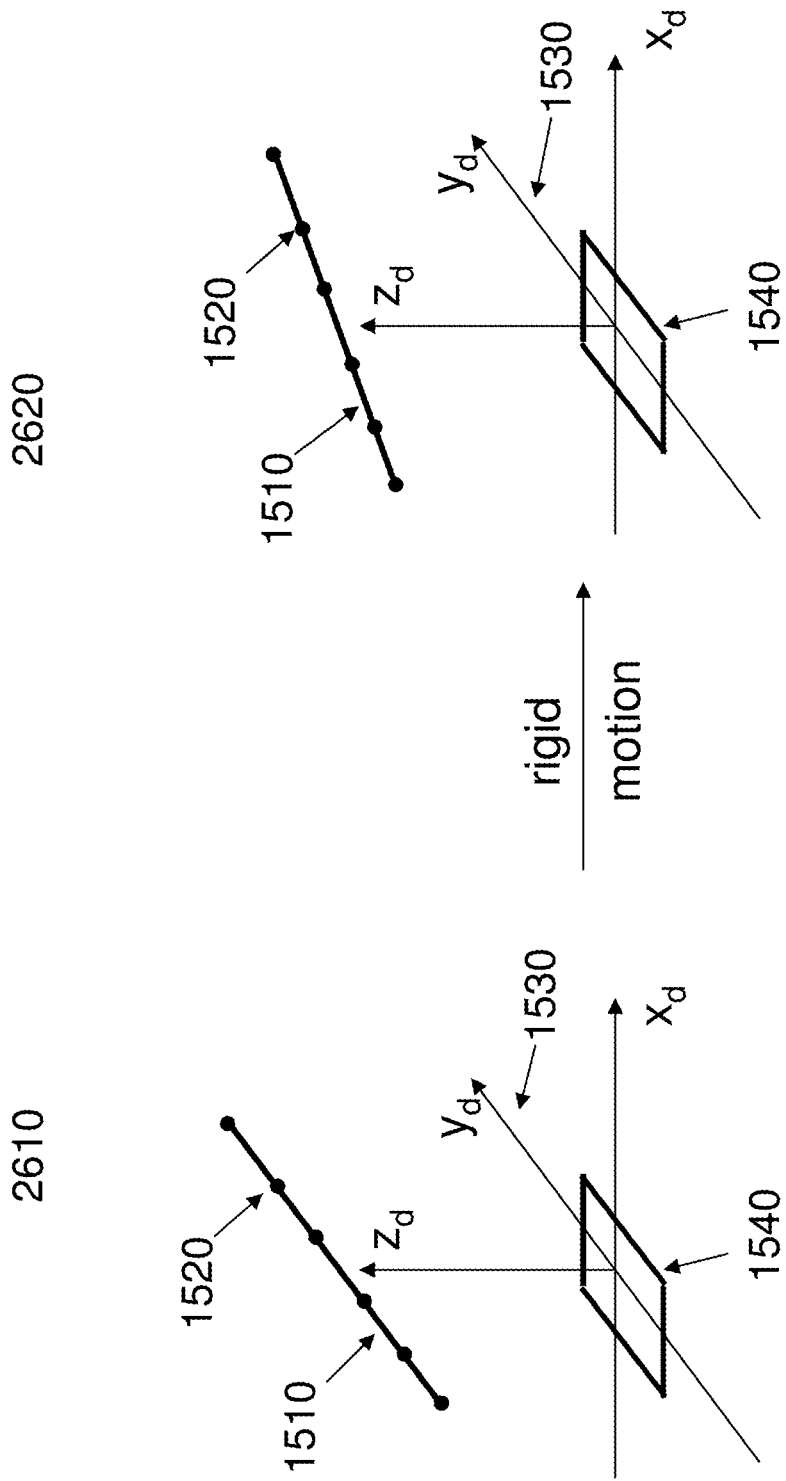
FIG. 16 is a diagram that schematically shows an exemplary resulting orientation and distance of a linear track x-ray source assembly after applying rigid motion to a starting orientation and distance of a linear track x-ray source assembly according to embodiments of the application.

The imaging parameters can be the set or some subset of x-ray source locations $\{xs_i, ys_i, zs_i\}$ relative to the stationary detector for each projection image used in the reconstruction. Alternatively, if the distances between the x-ray source locations are known, as described above, then the imaging parameters correspond to the relative orientation and distance between x-ray source assembly and the detector. This corresponds to determining the set or subset of rigid motion parameters that convert the assumed nominal x-ray source positions to the positions in space that optimize the reconstruction metric. FIG. 16 is a diagram that shows an exemplary resulting orientation and distance of a linear track x-ray source assembly 1620 after applying rigid motion to the starting orientation and distance of a linear track x-ray source assembly 1610. The set rigid motion parameters can be the rotations $\theta x$, $\theta y$, and $\theta z$ about and translations tx, ty, and tz along the detector's x, y, and z axes.

It should be noted especially for the case where the imaging parameters correspond to the set of x-ray source locations that a regularizer can be added to the reconstruction metrics that will enforce that the selected or optimized x-ray source locations $\{xs_i, ys_i, zs_i\}$ yield a smooth trajectory. An example of such a regularizer is the L2 norm of the set of x-ray source locations $$\sum_i |\nabla xs_i|^2 + |\nabla ys_i|^2 + |\nabla zs_i|^2.$$

In the update filtered projection operation block 1446, if the current updated imaging geometry is significantly different from the imaging geometry used to filter the projections then the projection can be filtered using the current updated imaging geometry. The updated filtered projections can then be used in the next iteration(s) of the imaging geometry auto-correction reconstruction algorithm.

Figure 18:
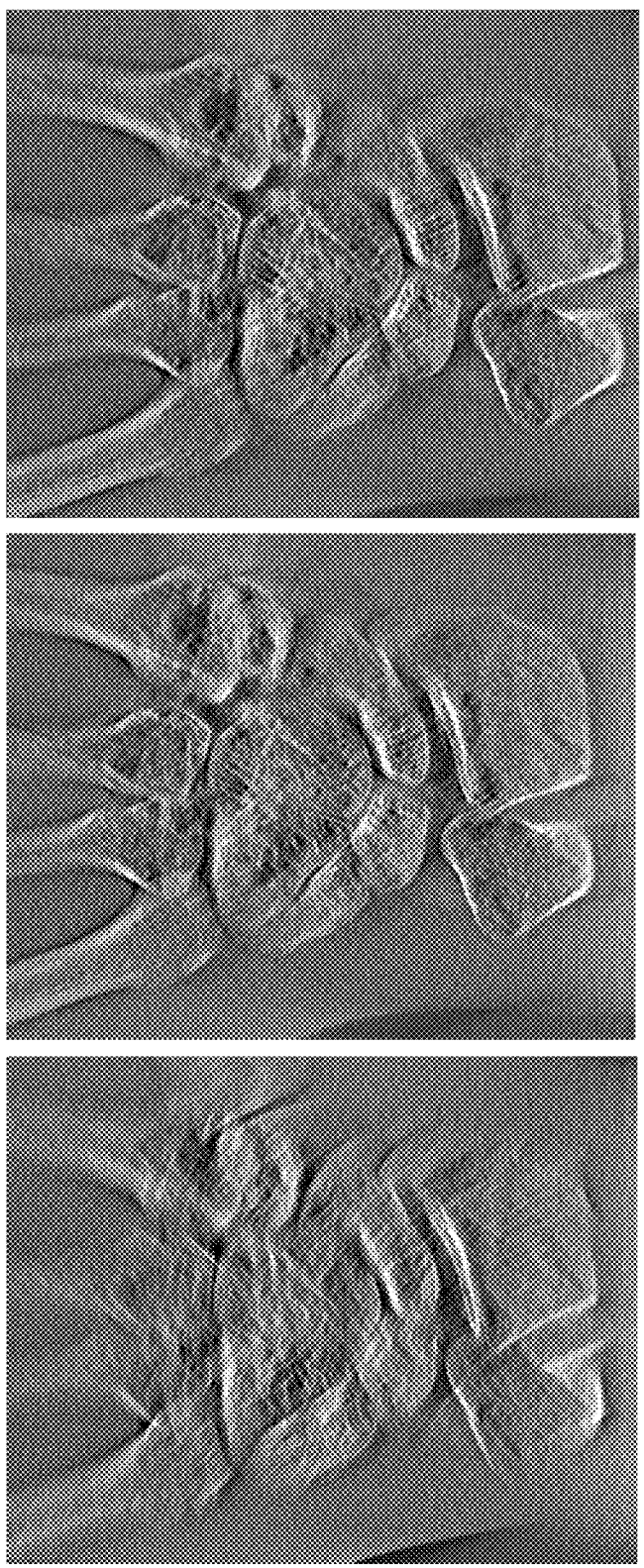
FIG. 18 is a diagram that shows a slice of the tomosynthesis reconstruction for an exemplary linear track scan using an assumed imaging geometry, a modified geometry as determined using imaging geometry auto-correction reconstruction, and an actual imaging geometry according to embodiments of the application.

FIG. 18 is a diagram that shows a slice of the tomosynthesis reconstruction for a linear track scan of a hand phantom using the assumed imaging geometry 1810, the optimized geometry 1820 as determined by one imaging geometry auto-correction reconstruction algorithm, and the actual imaging geometry 1830. For the assumed geometry the x-ray source assembly is translated 180 cm along the detector's z axis and has the same orientation as the detector 1610. The actual geometry corresponds to the linear track being rotated −3.9 degree about its x axis followed by a −3.9 degree rotation about its z axis from its assumed position. As shown in FIG. 18, tomosynthesis reconstruction results using the imaging geometry calculated from the auto-correction reconstruction algorithm and the actual imaging geometry are essentially indistinguishable.

Various exemplary embodiments described herein can illustrate individual modes of operation. In certain exemplary embodiments, more than one mode can be provided in/by a single mobile radiographic imaging system and/or methods for using the same.

Certain exemplary embodiments of mobile radiographic imaging systems and/or method for using the same can determine or use auto-correction reconstruction processes that can produce data in a unified coordinate system, for each image in a capture sequence that provides the relative x-ray source focal spot position and detector position and orientation. This information can have various multiple uses in tomosynthesis image reconstruction. For example, such information can be used in conjunction with X-ray exposure technique technical factors to estimate the signal the detector would receive with an "air exposure" (e.g., without any object/subject interposed between the source(s) and the detector). This "air exposure" image can be used in tomosynthesis reconstruction to provide the estimated linear attenuation coefficients for volumetric reconstruction processing. Further, a recovered geometry according to the application can also be used to apply tomosynthesis reconstruction approaches employing other methods such as SIRT, SART, ART or other methods known by those skilled in the art of volumetric reconstruction algorithms. In addition, recovered geometry can also be used in patient dose estimation.

FIG. 19 is a diagram that shows a mobile radiographic imaging systems that can include first and second (e.g., multiple) radiographic x-ray sources. As shown in FIG. 19, a mobile radiographic imaging system can include a first radiographic x-ray source and collimator, and a second x-ray source comprising a distributed source (e.g., rectangle) that can be either permanently attached or attached (detachable) when needed.

FIG. 20 is a diagram that shows a mobile radiographic imaging systems that can include first and second (e.g., multiple) radiographic x-ray sources. As shown in FIG. 20, a mobile radiographic imaging system can include a first radiographic x-ray source and collimator, and a second x-ray source comprising a distributed source attachment (e.g., linear) that can be either permanently attached or attached (detachable) when needed. In one embodiment, the distributed sources can be on a curved support to maintain a single distance from a corresponding point on a detector. Exemplary distributed source attachment can have a first position for use and a second position for storage (e.g., folded) when not used. In one embodiment, exemplary distributed source attachments can have a first position for use, at least one intermediate position (e.g., half-unfolded) and a second position for storage (e.g., folded) when not used. In one embodiment, such exemplary distributed sources can be replaced by a track and a moving x-ray source.

Consistent with at least one embodiment, exemplary methods can use a computer program with stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products of this application may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

Exemplary functions performed by the diagrams of FIGS. 14a-14b, the system processor or the mobile radiographic unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, central processing unit (CPU), arithmetic logic unit (ALU), GPU, video digital signal processor (VDSP) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software is generally executed from a medium or several media by one or more of the processors of the machine implementation.

Certain exemplary embodiments according to the application can provide method and/or apparatus that can include a moveable transport frame; a handle; an adjustable support structure coupled to the moveable transport frame; an x-ray source assembly mounted to the adjustable support structure configured to direct x-ray radiation towards a subject from a plurality of different source positions; control circuitry at the mobile x-ray radiography apparatus and coupled to the X-ray source assembly, the control circuitry configured to receive projection image data sets for the plurality of different source positions for reconstruction of tomosynthesis images.

Certain exemplary embodiments according to the application can provide method and/or apparatus for use in a mobile x-ray radiography apparatus that can include obtaining a plurality of x-ray tomosynthesis projection images of an object; and generating a three-dimensional reconstruction of the object using the x-ray projection images; where an imaging geometry of a plurality of x-ray source positions relative to a radiographic detection array is not known for the plurality of x-ray tomosynthesis projection images.

Certain exemplary embodiments according to the application can provide method and/or apparatus for digital radiographic 3D tomographic image reconstruction, executed at least in part on a computer, that can include obtaining image data for a plurality of 2D tomographic projection images over a range of scan angles; generating a three-dimensional reconstruction using the plurality of 2D tomographic projection images and a first imaging geometry for the plurality of 2D tomographic projection images; determining a tomographic reconstruction performance metric for a current three-dimensional reconstruction; comparing the tomographic reconstruction performance metric to a prescribed value; and setting the first imaging geometry to an adjusted imaging geometry and repeating the generating through setting operations when the tomographic reconstruction performance metric is not equivalent to the prescribed value, otherwise storing the current three-dimensional reconstruction and first imaging geometry in a computer-accessible memory.

For selected exemplary apparatus or method embodiments, an x-ray source can include at least one x-ray source assembly that can include a moveable source. In one embodiment, a moveable source is mounted to a support along which the x-ray source is configured to move. In one embodiment, a support can be generally linear, 2D track, a curve, a 3D path, or a plurality of supports. In one embodiment, a moveable source can include the moveable transport frame or the adjustable support structure. For selected exemplary apparatus or method embodiments, an X-ray source assembly can include a plurality of distributed sources in a prescribed spatial relationship. In one embodiment, a plurality of distributed sources can be mounted along a support. In one embodiment, a prescribed spatial relationship is one or more linear tracks, 2D tracks, curves, rectangles or 3D paths. In one embodiment, a moveable transport frame or the adjustable support structure can be configured to position the x-ray source at the plurality of different source positions. For selected exemplary apparatus or method embodiments, tomosynthesis images are three dimensional. For selected exemplary apparatus or method embodiments, an initial projection image for an object is taken before the projection image data sets for the plurality of different source positions are obtained.

For selected exemplary apparatus or method embodiments, imaging geometry can include geometry of a movable x-ray source and an x-ray detector. In one embodiment, an imaging geometry comprises a position of a detector relative to an x-ray source or position the x-ray source relative to the detector. In one embodiment, an imaging geometry comprises a position and orientation of an x-ray detector, and a position and orientation of an x-ray source for each of the plurality of different source positions. In one embodiment, a position of an x-ray source is determined in the imaging geometry. In one embodiment, a position of an x-ray detector is determined relative to a coordinate system of the x-ray source. In one embodiment, an imaging geometry comprises a system imaging geometry, an imaging geometry of an x-ray source, and/or an imaging geometry of an x-ray detector. In one embodiment, an imaging geometry comprises a position and orientation of an x-ray detector, and a position and orientation of an x-ray source for each of the plurality of different source positions. In one embodiment, the position and orientation of the detector is determined to change at least once among the plurality of different source positions. In one embodiment, an imaging geometry comprises an x-ray source assembly that includes a moveable source, where the moveable source comprises at least one x-ray source is mounted to a support along which the at least one x-ray source is configured to move or comprises a plurality of distributed sources in a prescribed spatial relationship. In one embodiment, an initial projection image for an object is taken before the image data for a plurality of 2D tomographic projection images over a range of scan angles is obtained. In one embodiment, an initial projection image for an object is taken before the obtaining step to align the system, where the tomographic reconstruction performance metric is less than or over a preset threshold. In one embodiment, an initial projection image is from a central or near central one of multiple distributed sources or at an intermediate position in a moving path for a x-ray source. For selected exemplary apparatus or method embodiments, a tomographic reconstruction performance metric is an image quality metric or a data fidelity metric For selected exemplary apparatus or method embodiments, a portable power supply can power a moveable transport frame, control circuitry and/or the x-ray source. For selected exemplary apparatus or method embodiments, a portable digital detector assembly (grid) is configured to receive the radiation from the source and to remain stationary or move during receipt of the radiation from the plurality of different source positions, where an X-ray source assembly and the detector assembly include sensors and/or transmitters cooperatively arranged to detect distance and orientation of the X-ray source assembly and detector assembly with respect to one another. In one embodiment, the detector is wirelessly coupled to control circuitry for transmitting image data to the control circuitry and/or control signals from the control circuitry to the detector. In one embodiment, a portable human interface device is coupled to the control circuitry; the control circuitry is configured to transmit the projection image data sets to a remote system for computation of tomosynthesis. For selected exemplary apparatus or method embodiments, source positions form a first angle of between approximately 5 and 120 degrees or form a second angle of between approximately 20 and 40 degrees with respect to a detector. In one embodiment, an imaging geometry of an x-ray source is determined, comprising determining a position of an x-ray detector in the imaging geometry of the x-ray source. In one embodiment, after an imaging geometry of the plurality of different source positions is determined, comprising determining a position of an x-ray detector in the imaging geometry of the plurality of different source positions. For selected exemplary apparatus or method embodiments, an x-ray detector captures 2-30 frames per second over a 1-20 second imaging interval or captures 3-5 frames per second over a 1-3 second imaging interval. For selected exemplary apparatus or method embodiments, a plurality of tomographic projection images comprises 30-60 images or 25-100 images. For selected exemplary apparatus or method embodiments, a central X-ray source or an additional x-ray source has sufficient X-ray power to capture standard projection radiography images or provide up to a 120 kVp exposure.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Priority is claimed from commonly assigned, copending U.S. provisional patent applications Ser. No. (a) 61/728,401, filed Nov. 20, 2012, entitled "ACQUISITION SCAN GEOMETRY CORRECTIONS FOR TOMOSYNTHESIS APPARATUS AND METHODS FOR MOBILE RADIOGRAPHIC APPARATUS", in the name of Richard A. Simon et al., the disclosure of which is incorporated by reference.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

Embodiments disclosed herein can be related to pending U.S. patent application Ser. No. 13/283,654, Alignment Apparatus for X-ray Imaging System, the disclosure of which is incorporated by reference in its entirety.

The invention claimed is:

1. A method of using a mobile x-ray radiography system having one or more x-ray sources and a digital radiographic detector, the method comprising:
   rolling the mobile x-ray radiography system to an imaging location;
   moving the one or more x-ray sources over a range of vertical and horizontal positions to an imaging position;
   obtaining a plurality of x-ray projection images of an object using the one or more x-ray sources and the digital radiographic detector; and
   generating a three-dimensional reconstructed image of the object using the obtained plurality of x-ray projection images, including recovering an imaging geometry of the one or more x-ray sources and the digital radiographic detector using a computer programmed iterative method.

2. The method of claim 1, further comprising moving the one or more x-ray sources to a plurality of different x-ray source positions during the step of obtaining.

3. The method of claim 1, further comprising not using a measurable orientation of the detector and an orientation of the one or more x-ray sources for the step of recovering the imaging geometry.

4. The method of claim 1, wherein the step of obtaining a plurality of x-ray projection images includes activating in a prescribed sequence the one or more x-ray sources.

5. The method of claim 1, further comprising without using a measurable relative spatial geometry of the one or more x-ray sources and the digital radiographic detector for the step of recovering the imaging geometry.

6. A method for digital radiographic 3D tomographic image reconstruction of a subject, the method executed at least in part on a computer, the method comprising:
   generating a three-dimensional reconstructed image of the subject using a plurality of 2D tomographic projection images of the subject and an estimate of an imaging geometry of an x-ray source and a digital detector that were used to obtain the plurality of 2D tomographic projection images of the subject;
   determining a tomographic reconstruction performance metric for the digital radiographic 3D tomographic image reconstruction of the subject;
   comparing the tomographic reconstruction performance metric to a stopping criterion, including ascertaining whether the tomographic reconstruction performance metric satisfies the stopping criteria; and
   adjusting a current imaging geometry estimate to an adjusted imaging geometry estimate and repeating the steps of generating, determining, comparing, and adjusting if the tomographic reconstruction performance metric is ascertained to not satisfy the stopping criterion, or storing a current three-dimensional reconstructed image of the subject and the current imaging geometry estimate in a computer-accessible memory if the tomographic reconstruction performance metric is ascertained to satisfy the stopping criterion.

7. The method of claim 6, further comprising mounting an x-ray source assembly to a support and moving at least one x-ray source of the x-ray source assembly along the support to obtain the plurality of 2D tomographic projection images of the subject.

8. The method of claim 6, further comprising capturing an initial projection image of the subject before obtaining the plurality of 2D tomographic projection images of the subject, the method further comprising obtaining the plurality of 2D tomographic projection images of the subject over a range of angles.

9. The method of claim 8, further comprising aligning the x-ray source and the detector, and capturing the initial projection image of the subject using a multiple distributed x-ray source assembly, including activating a centrally positioned one of the x-ray sources in the x-ray source assembly.

10. The method of claim 6, further comprising ascertaining that the tomographic reconstruction performance metric satisfies the stopping criteria if the tomographic reconstruction performance metric converges to a prescribed value, a relative change in the tomographic reconstruction performance metric falls below a prescribed threshold, or the step of repeating is performed for a preset number of iterations.

11. The method of claim 6, further comprising defining the tomographic reconstruction performance metric as an image quality metric or a data fidelity metric.

12. The method of claim 6, further comprising moving the digital detector to obtain the plurality of 2D tomographic projection images of the subject.

13. The method of claim 6, further comprising providing an x-ray source having sufficient X-ray power to capture standard projection radiography images up to a 120 kVp exposure.

14. The method of claim 6, further comprising providing an x-ray source assembly having a plurality of distributed x-ray sources in a prescribed spatial relationship and activating in a prescribed sequence two or more of the plurality of distributed x-ray sources.

15. The method of claim 6, further comprising adjusting exposure positions of the x-ray source between approximately 5 and 120 degrees.

16. The method of claim 6, further comprising capturing the 2D tomographic projection images at a rate of 2-30 frames per second over a 1-20 second imaging interval using the digital detector.

17. The method of claim 6, further comprising capturing about 30-60 2D tomographic projection images of the subject for the step of generating the three-dimensional reconstructed image of the subject.

* * * * *

UNITED STATES PATENT AND TRADEMARK OFFICE
CERTIFICATE OF CORRECTION

PATENT NO. : 9,649,074 B2
APPLICATION NO. : 14/435272
DATED : May 16, 2017
INVENTOR(S) : Richard A. Simon et al.

It is certified that error appears in the above-identified patent and that said Letters Patent is hereby corrected as shown below:

On the Title Page

Item (73) Assignee should read --Carestream Health, Inc.--

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*